(12) United States Patent
Balian

(10) Patent No.: US 7,871,978 B2
(45) Date of Patent: Jan. 18, 2011

(54) BONE TROPIC PEPTIDES

(75) Inventor: Garabed Balian, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 514 days.

(21) Appl. No.: 11/666,940

(22) PCT Filed: Nov. 4, 2005

(86) PCT No.: PCT/US2005/040191

§ 371 (c)(1),
(2), (4) Date: May 3, 2007

(87) PCT Pub. No.: WO2006/052840

PCT Pub. Date: May 18, 2006

(65) Prior Publication Data

US 2008/0214468 A1    Sep. 4, 2008

Related U.S. Application Data

(60) Provisional application No. 60/624,957, filed on Nov. 4, 2004, provisional application No. 60/695,325, filed on Jun. 30, 2005.

(51) Int. Cl.
*A61K 38/28* (2006.01)
*C07K 14/62* (2006.01)
(52) U.S. Cl. ..................................... 514/5.9
(58) Field of Classification Search .................. None
See application file for complete search history.

(56) References Cited

U.S. PATENT DOCUMENTS

| 5,683,459 | A | 11/1997 | Brekke | |
|---|---|---|---|---|
| 6,541,024 | B1 * | 4/2003 | Kadiyala et al. | 424/426 |
| 7,323,542 | B2 * | 1/2008 | Balian | 530/300 |
| 2003/0092077 | A1 | 5/2003 | Ramarao | |
| 2003/0113714 | A1 | 6/2003 | Belcher et al. | |
| 2003/0166004 | A1 | 9/2003 | Gyuris et al. | |
| 2004/0171552 | A1 | 9/2004 | Peled et al. | |
| 2005/0085623 | A1 | 4/2005 | Balian et al. | |

FOREIGN PATENT DOCUMENTS

| WO | WO 02/02593 | A2 | 1/2002 |
|---|---|---|---|
| WO | WO 03/072593 | * | 9/2003 |

OTHER PUBLICATIONS

Christian et al. Nucleolin expressed at the cell surface is a marker of endothelial cells in angiogenic blood vessels. JCB, Nov. 24, 2003, pp. 871-878.*
Sporn et al. Chemoprevention of cancer. Carcinogenesis. 2000. vol. 21, No. 3, pp. 525-530.*
Bab et al. Histone H4-related osteogenic growth peptide (OGP): a novel circulating stimulator of osteoblastic activity. The EMBO Journal. 1992. vol. 11, Nol. 5, pp. 1867-1873.*

* cited by examiner

*Primary Examiner*—Cecilia Tsang
*Assistant Examiner*—Marcela M Cordero Garcia
(74) *Attorney, Agent, or Firm*—Rodney L. Sparks

(57) ABSTRACT

The present invention is directed to the use of bone tropic peptides identified through the use of a phage display library. More particularly, the invention is directed to compositions comprising the bone tropic peptides and methods for using such compositions to regulate osteogenesis, cell adhesion and angiogenesis, and diseases and disorders thereof, and to inhibit cancer cell metastasis and growth.

5 Claims, 10 Drawing Sheets

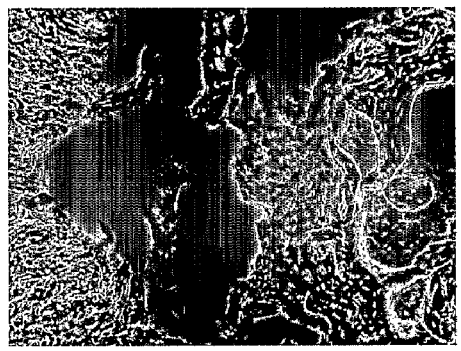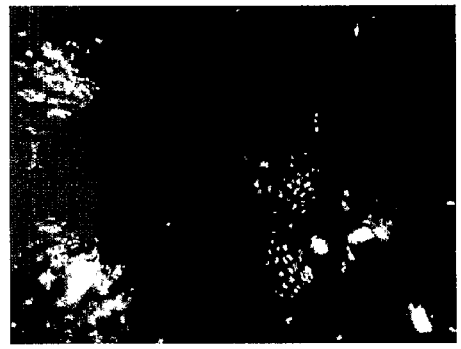
FIG. 7A  FIG. 7B
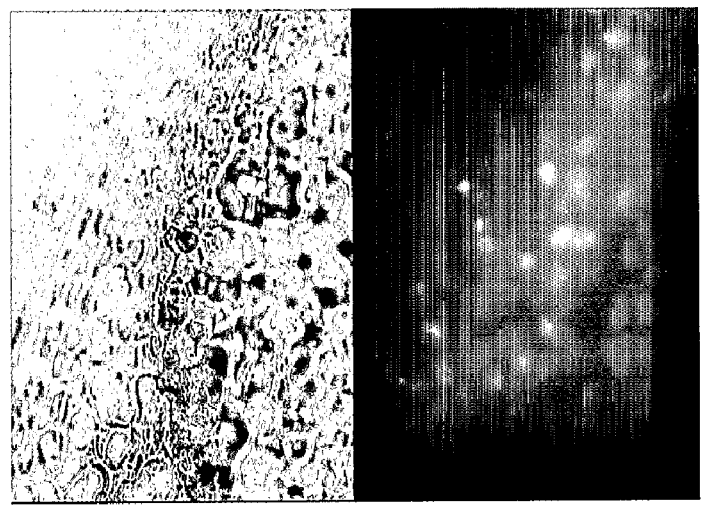
FIG. 7C   FIG. 7D

BONE TROPIC PEPTIDES

CROSS REFERENCE TO RELATED APPLICATIONS

This application is a national stage filing of International Application No. PCT/US2005/040191, filed on Nov. 4, 2005, which claims priority under 35 U.S.C. §119(e) to U.S. Provisional Application Ser. Nos. 60/624,957 filed Nov. 4, 2004 and 60/695,325 filed Jun. 30, 2005, the disclosures of which are incorporated herein by reference.

STATEMENT REGARDING FEDERALLY SPONSORED RESEARCH OR DEVELOPMENT

This invention was made with United States Government support under Grant Nos. GG10518 and DAMD 17-03-1-0043 awarded by the Department of Defense. The United States Government may have certain rights in the invention.

FIELD OF THE INVENTION

The present invention is directed to the use of bone tropic peptides identified through the use of a phage display library. More particularly, the invention is directed to compositions comprising the bone tropic peptides and methods for using such compositions to regulate cell adhesion, angiogenesis, and osteogenesis. Furthermore, the peptides are useful to treat diseases and disorders related to abnormal cell adhesion, angiogenesis, and osteogenesis.

BACKGROUND OF THE INVENTION

A limited number of proteins have been identified as being primarily associated with bone tissue. In addition, reports in the literature have presented compelling evidence that the targets of these proteins are receptors on the cell surface. Protein domains may be responsible for targeting these proteins to cell receptors or receptor ligands in the extracellular matrix of the target tissue. Therefore, these peptides could be used for a wide variety of therapeutic uses including the delivery of drugs that could help in the treatment of musculoskeletal disorders, genetic or acquired, osteoporosis and metastatic cancer. Furthermore, it is anticipated that the peptides themselves can serve as therapeutic agents providing osteogenic or tropic activity for osteoblast, mesenchymal or hematopoietic cell lineages.

Although much progress has been made in the field of bone regenerative medicine during the past few years, current therapies that use bone grafts still have their limitations. In spite of the fact that material science technology has lead to clear improvements in the field of bone repair, no adequate bone substitute has been developed and hence injuries that produce large bone defects still represent a major challenge for orthopedic and reconstructive surgeons. Delivery of osteoinductive factors, such as bone morphogenetic proteins (BMPs), has been successfully applied to augment local bone repair and several formulations are available for clinical applications. However, the wide-spread clinical efficacy of these treatments continues to be hampered by inadequate delivery of carriers, release kinetics, dosage and potency.

It is clear that an adequate bone replacement is yet to be found and that it is needed for full recovery of large bone defect. Phage display peptide libraries have enabled the discovery of peptides that selectively target specific organs. Much progress has been made in this rapidly developing field and many possible applications of phage technology have been developed. These include the creation and screening of libraries to discover novel therapeutic targets and methods for selection of biologically active ligands.

Approximately 5% to 10% of fractures sustained in the United States are associated with delayed healing or non-union. Impaired fracture-healing is associated with a number of risk factors, including poor blood supply, associated soft-tissue injury, extensive bone loss, instability, infection, poor general medical condition, and unhealthy habits, such as smoking. Traditionally, problems related to fracture-healing have been treated with operative intervention, which often involves the use of an autogenous bone graft. However, bone graft-harvesting procedures are associated with a morbidity rate of 10% to 30%, and only limited amounts of autogenous bone are available. Allograft provides an osteoconductive scaffold but lacks osteoinductive properties. There is also a concern about possible disease transmission. Therefore, alternative strategies designed to enhance the healing of acute fractures and to improve the treatment of delayed unions and nonunions are required.

A number of growth factors are expressed during different phases of experimental fracture-healing. Both in vitro and in vivo studies have shown that growth factors, such as transforming growth factor beta (TGF-β), bone morphogenetic protein (NMP), fibroblast growth factor (FGF), platelet-derived growth factor (PDGF) and insulin-like growth factor (IGF), have varying amounts of osteoinductive potential. Among these growth factors, BMPs appear to have the most osteoinductive potential. The BMPs are members of the TGF-β superfamily, and more than a dozen different molecules have been identified at this time. Presently, BMP-2, 4, and 7 are known to play a critical role in bone-healing by virtue of their ability to stimulate differentiation of mesenchymal cells to an osteochondroblastic lineage.

It is believed that synthetic peptides have several advantages over large molecular growth factor proteins: (1) they can be synthesized on a large scale at a relatively low cost and with little variation between different batches; (2) they are more stable than large-molecule growth factors and easier to handle; (3) they have long shelf lives, both as free and as immobilized peptides, and do not require special handling and storage procedures or facilities; (4) the peptides and their biomaterial composites can be sterilized easily by autoclaving, by UV, or by gamma-irradiation; and (5) they do not induce inflammatory responses in vivo.

Biologically, the peptides may have other advantages, among the most relevant of which is a broad potential for bioengineering applications. They could be used to reduce the effective dose of growth factors within a medical device and could be of particular use for coating onto device surfaces. They could also maximize the biological activity of biological preparations such as demineralized bone matrix (DMB). Furthermore, they peptides might augment the endogenous levels of growth factors generated by host tissue during bone healing. The discovery of osteogenic peptides therefore may open up a wide variety of practical applications for the treatment of fracture non-unions or of bone defects.

Recently, the osteogenic growth peptide (OGP) and its analogues, such as OGP-14, have attracted considerable clinical interest. OGP is a naturally occurring tetradecapeptide identical to the C-teiniinal amino acid sequence comprising residues 89-102 of histone H4. OGP and its analogues increase bone formation and trabecular bone density and stimulate fracture healing when administered to mice and rats. In cultures of osteoblastic and other bone marrow stromal cells derived from human and other mammalian species, OGP regulates proliferation, alkaline phosphatase activity, and matrix mineralization. The thrombin-related peptide, TP508, is a 23 amino acid peptide representing the natural amino acid sequence of the receptor-binding domain of human thrombin. P-15 is a 15-residue synthetic analogue of a cell-binding domain of type I collagen. Both of these peptides have the ability to enhance bone regeneration in rodents, however, they are not bone targeting peptides and do not modify osteogenesis directly. TP508 promotes bone regeneration by stimulating revascularization of granulation tissue at the injured site, while P15 mimics the cell binding domain of type I collagen, which is an extracellular matrix protein with multiple cell-binding domains for osteogenic progenitor cells, to play a role in osteogenesis.

Random peptide phage display libraries have been used in vivo with nonrandom distribution of peptides isolated from phage bound to different organs. This specificity of phage binding as imparted by the peptide epitope has allowed investigators to determine that each organ's microvasculature had unique determinants. The process of in vivo phage display has led to the identification of interacting receptors on cells. In addition to the cell surface targets that were found for phage display peptides, there have been reports of an intracellular fate for phage display vectors in mammalian cells.

These observations have raised the possibility that peptides identified by in vivo biopanning of a phage display library may be useful for targeted delivery of genes for therapeutic purposes and perhaps for their delivery to cells in specific organs. Furthermore, peptides that are directed to cell surface components, such as CD34 may prove useful for cell selection. Screening the phage library can lead to the identification of ligands to cell surface proteins in target cells and tissues. Since the construction of the peptide phage display library is random by design, many of the peptides that interact specifically with any given target tissue may not represent true protein epitopes but are likely to be protein mimotopes. These sequences from phage display libraries may be helpful as structural and functional mimics that could serve as the basis for novel drug design for the interacting target. In vivo biopanning has been used to identify peptides that exhibit organ-specific homing for the kidney and brain and later for other organs and tumor vasculature in animals.

There is a long felt need in the art to identify peptides useful to treat diseases and disorders related to abnormal cell adhesion, angiogenesis, and osteogenesis. The present invention satisfies these needs.

SUMMARY OF THE INVENTION

The present invention is directed to the use of a series of peptides that have been discovered to exhibit bone targeting properties. Compositions comprising these proteins have utility in regulating cell adhesion, angiogenesis and osteogenesis. The present invention also discloses that peptides of the invention localize to the marrow of bone. Furthermore these compounds can be coupled with other bioactive compounds as a means of delivering or retaining therapeutic agents at their target sites. In accordance with one embodiment, the bone targeting peptides of the present invention are combined with a biodegradable carrier that is capable of releasing the peptides in a predictable and controlled rate.

The present invention is directed to the use of peptides that target bone and bone marrow, regulate cell adhesion, regulate angiogenesis, regulate angiogenesis, as well as methods for using biocompatible compositions comprising these peptides for treating disorders and diseases of these functions. The bone targeting peptides were identified using a phage display library based on their ability to bind and become localized to bone tissue after general injection into a mouse. In one aspect, the peptides of the invention have attached a Gly-Gly-Gly-Ser linker. Accordingly, one aspect of the present invention is directed to the use of purified peptides comprising the following sequences:

(SEQ ID NO: 1) (L1)
THR-MET-ARG-ASN-PRO-ILE-THR-SER-LEU-ILE-SER-VAL-GLY-GLY-GLY-SER, (SEQ ID NO: 2) (L2)
LEU-LEU-ALA-ASP-THR-THR-HIS-HIS-ARG-PRO-TRP-THR-GLY-GLY-GLY-SER, (SEQ ID NO: 3) (L5)
LYS-GLU-ILE-PRO-PRO-ILE-PRO-LEU-LEU-ALA-PRO-SER-GLY-GLY-GLY-SER, (SEQ ID NO: 4) (L6)
ASN-ASN-VAL-SER-GLN-LYS-TRP-GLN-GLN-ARG-LEU-ILE-GLY-GLY-GLY-SER, (SEQ ID NO: 5) (L7)
ASN-SER-MET-ILE-ALA-HIS-ASN-LYS-THR-ARG-MET-HIS-GLY-GLY-GLY-SER, (SEQ ID NO: 6) (L11)
GLY-ILE-HIS-VAL-PRO-TRP-MET-PRO-PRO-VAL-ALA-PHE-GLY-GLY-GLY-SER, (SEQ ID NO: 7) (L12)
GLN-ARG-SER-TRP-THR-LEU-ASP-SER-ALA-LEU-SER-MET-GLY-GLY-GLY-SER, (SEQ ID NO: 8) (L13)
SER-GLY-HIS-GLN-LEU-LEU-LEU-ASN-LYS-MET-PRO-ASN-GLY-GLY-GLY-SER, (SEQ ID NO: 9) (L14)
SER-SER-THR-LEU-LYS-THR-PHE-PHE-GLY-PHE-PRO-ASP-GLY-GLY-GLY-SER, (SEQ ID NO: 10) (L19)
ASP-SER-SER-ASN-PRO-ILE-PHE-TRP-ARG-PRO-SER-SER-GLY-GLY-GLY-SER, (SEQ ID NO: 11) (R1)
ASN-TYR-SER-HIS-LEU-ARG-VAL-LYS-LEU-PRO-THR-PRO-GLY-GLY-GLY-SER, (SEQ ID NO: 12) (R2)
SER-GLY-HIS-GLN-LEU-LEU-LEU-ASN-LYS-MET-PRO-ASN-GLY-GLY-GLY-SER, (SEQ ID NO: 13) (R3)
ALA-THR-TRP-SER-HIS-HIS-LEU-SER-SER-ALA-GLY-LEU-GLY-GLY-GLY-SER, (SEQ ID NO: 14) (R8)
SER-TYR-SER-GLN-MET-ASP-PRO-PRO-ARG-SER-LEU-PRO-GLY-GLY-GLY-SER, (SEQ ID NO: 15)
THR-MET-ARG-ASN-PRO-ILE-THR-SER-LEU-ILE-SER-VAL,

-continued (SEQ ID NO: 16)
LEU-LEU-ALA-ASP-THR-THR-HIS-HIS-ARG-PRO-TRP-THR, (SEQ ID NO: 17)
LYS-GLU-ILE-PRO-PRO-ILE-PRO-LEU-LEU-ALA-PRO-SER, (SEQ ID NO: 18)
ASN-ASN-VAL-SER-GLN-LYS-TRP-GLN-GLN-ARG-LEU-ILE, (SEQ ID NO: 19)
ASN-SER-MET-ILE-ALA-HIS-ASN-LYS-THR-ARG-MET-HIS, (SEQ ID NO: 20)
GLY-ILE-HIS-VAL-PRO-TRP-MET-PRO-PRO-VAL-ALA-PHE, (SEQ ID NO: 21)
GLN-ARG-SER-TRP-THR-LEU-ASP-SER-ALA-LEU-SER-MET, (SEQ ID NO: 22)
SER-GLY-HIS-GLN-LEU-LEU-LEU-ASN-LYS-MET-PRO-ASN, (SEQ ID NO: 23)
SER-SER-THR-LEU-LYS-THR-PHE-PHE-GLY-PHE-PRO-ASP, (SEQ ID NO: 24)
ASP-SER-SER-ASN-PRO-ILE-PHE-TRP-ARG-PRO-SER-SER, (SEQ ID NO: 25)
ASN-TYR-SER-HIS-LEU-ARG-VAL-LYS-LEU-PRO-THR-PRO, (SEQ ID NO: 26)
SER-GLY-HIS-GLN-LEU-LEU-LEU-ASN-LYS-MET-PRO-ASN, (SEQ ID NO: 27)
ALA-THR-TRP-SER-HIS-HIS-LEU-SER-SER-ALA-GLY-LEU, (SEQ ID NO: 28)
SER-TYR-SER-GLN-MET-ASP-PRO-PRO-ARG-SER-LEU-PRO, (SEQ ID NO: 29) (D1P1)
LEU-PRO-TRP-THR-GLU-PRO-SER-PHE-TRP-ARG-THR-PRO-
GLY-GLY-GLY-SER,
and (SEQ ID NO: 30)
LEU-PRO-TRP-THR-GLU-PRO-SER-PHE-TRP-ARG-THR-PRO, as well as bioactive homologs, fragments, and derivatives of SEQ ID NOs: 1-30 that exhibit bone targeting properties. Homologs and derivatives of SEQ ID NOs: 1-30 include amino acid sequences that differ from those sequences either by one or more conservative amino acid substitutions, or by one amino acid deletion, addition, or substitution. In one embodiment, the peptides comprise a sequence identical to SEQ ID NOs: 1-30, or differ from SEQ ID NOs: 1-30 by 1-2 conservative amino acids.

The sequences of the first 14 SEQ ID NOs: (SEQ ID NOs:1-14) are identical with the sequences of the peptides of the last 14 SEQ ID NOs: (SEQ ID NOs:15-28), except that each of the first 14 sequences have a carboxy terminal linker attached, wherein said linker is four amino acid residues, the first three residues of which are glycine and the fourth of which is serine. The sequences also have names used herein, said names being provided in parentheses next to each of the SEQ ID NOs: of the first fourteen sequences, as well as in the Examples (see Table 5). Therefore, SEQ ID NO:1 and SEQ ID NO:15 have the same base sequence, but SEQ ID NO:1 also has the carboxy terminal linker described above, wherein said linker is four amino acid residues. the first three residues of which are glycine and the fourth of which is serine. The same relationship is true for SEQ NOs:2 and 16, 3 and 17, 4 and 18, 5 and 19, 6 and 20, 7 and 21, 8 and 22, 9 and 23, 10 and 24, 11 and 25, 12 and 26, 13 and 27, and 14 and 28.

Another peptide of the invention has the sequences of SEQ ID NOs:29 and 30, and homologs, derivatives, and fragments thereof, and represent the peptide called D1P1 herein. The sequence for D1P1, with and without the four amino acid linker, is:

(SEQ ID NO: 29)
LEU-PRO-TRP-THR-GLU-PRO-SER-PHE-TRP-ARG-THR-PRO-
GLY-GLY-GLY-SER,
and (SEQ ID NO: 30)
LEU-PRO-TRP-THR-GLU-PRO-SER-PHE-TRP-ARG-THR-PRO.

Bone marrow mesenchymal stem cells (MSCs) are multipotential. This property makes them a suitable candidate for studying the events of bone formation and the effects of drugs and hormones on bone for the treatment of osteoporosis and metastatic disease.

In one aspect, the invention provides a method of inhibiting cancer cell growth, comprising administering a peptide of the invention.

In one aspect, the invention comprises a method of inhibiting cell adhesion.

In one aspect, the invention comprises a method of inducing release of adherent cells.

In one aspect, the invention provides a method of stimulating osteogenesis. In one aspect, the osteogenesis occurs during bone repair.

In one aspect, the invention provides a method of identifying a binding partner of a bone-targeting peptide of the invention.

In one aspect, the invention provides isolated nucleic acids comprising nucleic acid sequences which encode peptides of the invention.

In one aspect, the invention provides antibodies directed against the peptides of the invention.

In another aspect, the invention provides a kit for administering peptides of the invention.

BRIEF DESCRIPTION OF THE DRAWINGS

FIG. 5, comprising

FIG. 7, comprising FIGS. 7A, B, C, and D, represents photomicrographs of cryosections of bone incubated with biotinylated L13 (SEQ ID NO: 8) followed by FITC-labeled avidin. L13 binding to cells in bone and marrow sections (panel B) and rib (panel D) were visualized by phase contrast/bright microscopy (panels A and C) and epiluminescence microscopy for fluorescence (panels B and D). 40× magnification.

DETAILED DESCRIPTION OF THE INVENTION

Abbreviations

Figure 1A:
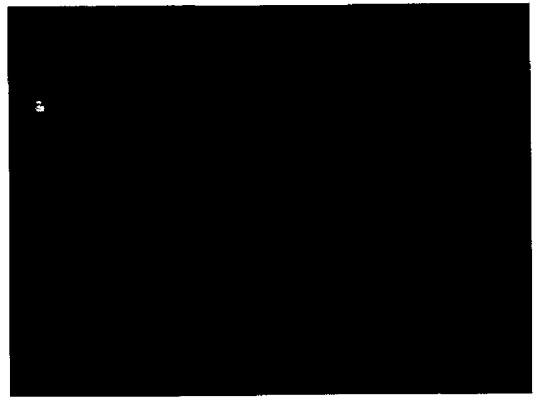
FIG. 1, comprising six panels, represents immunofluorescent micrographs of femoral bone incubated with PBS (upper panels), the peptide L7 (SEQ ID NO:5) (middle panels), and the peptide R1 (SEQ ID NO:11) (lower panels)
Figure 1B:
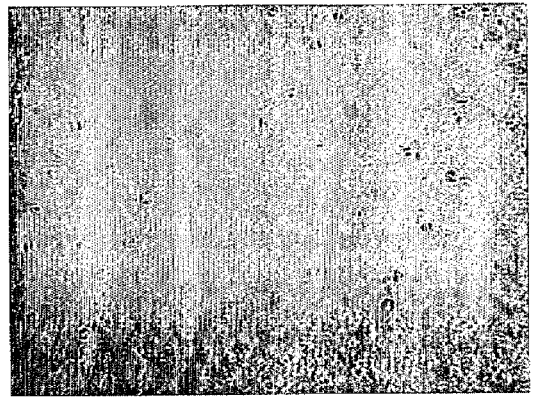
Figure 1C:
Figure 1D:
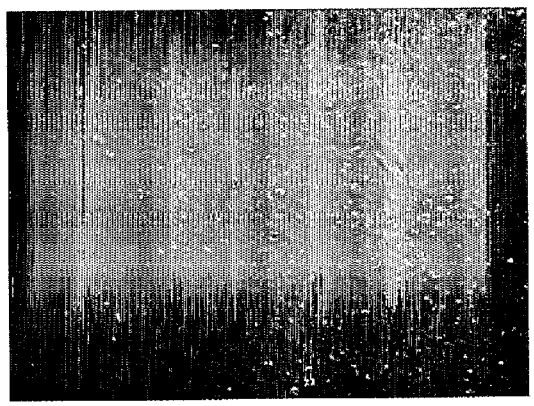
Figure 1E:
Figure 1F:
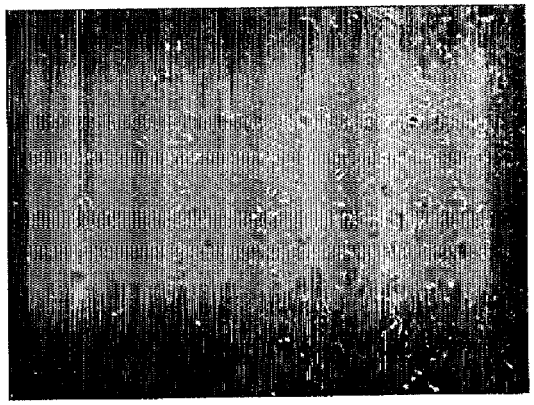
Figure 2A:
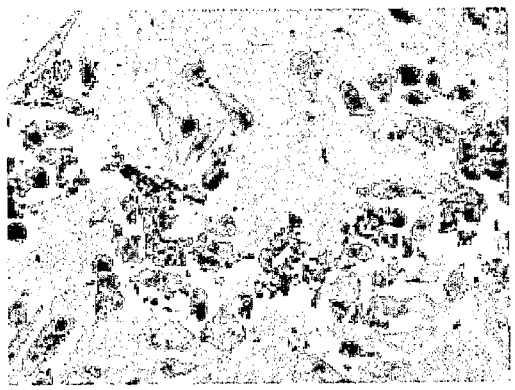
FIG. 2, comprising fours sets of 2 panels each (2A, B, C, D, E, F, G, and H) is a representation of micrographs demonstrating bovine aortic endothelial cells treated with the peptides L7 (SEQ ID NO:5), L12 (SEQ ID NO:7), L1 (SEQ ID NO:1), and L5 (SEQ ID NO:3) in the presence of fibronectin.
Figure 2B:
Figure 2C:
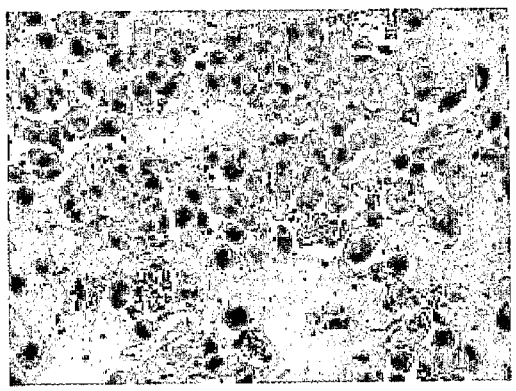
Figure 2D:
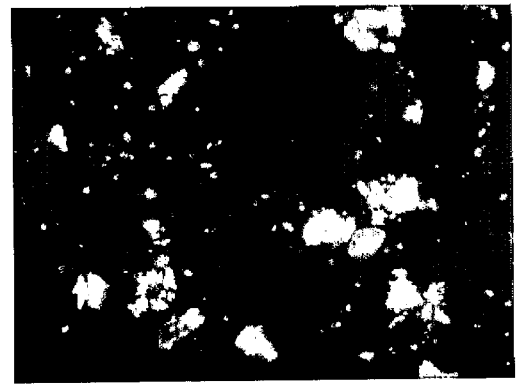
Figure 2E:
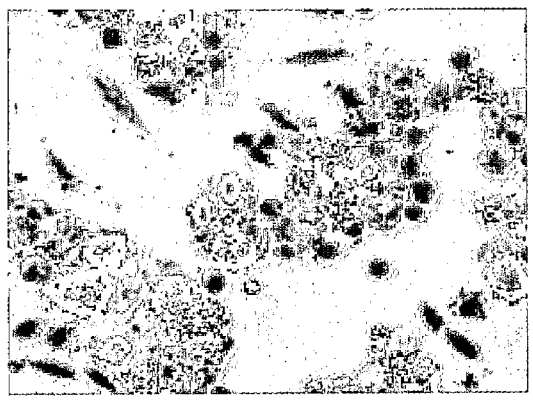
Figure 2F:
Figure 2G:
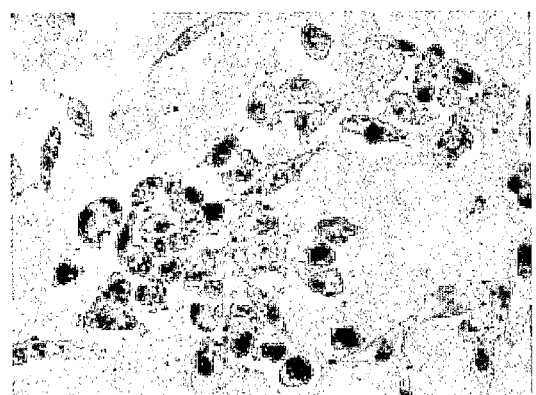
Figure 2H:
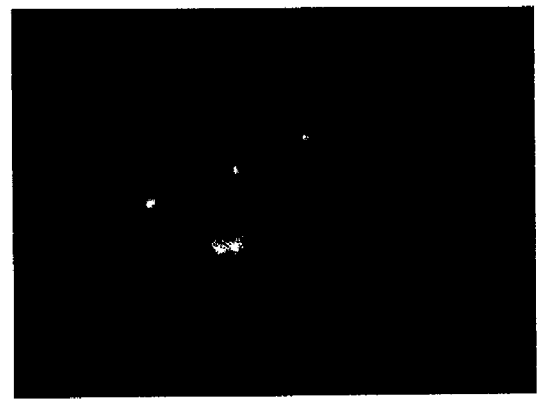

BAEC means bovine aortic endothelial cells
BSA means bovine serum albumin
FITC means fluorescein-isothiocyanate
HBME means human bone marrow endothelial cell
HE means hematoxylin/eosin
PBS means phosphate-buffered saline Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "adhesion", as used herein, refers broadly to a cell attaching to another cell, molecule, or other substrate.

As used herein, the term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, are reduced.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

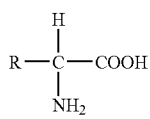

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "antisense oligonucleotide" means a nucleic acid polymer, at least a portion of which is complementary to a nucleic acid which is present in a normal cell or in an affected cell. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No. 5,034,506; Nielsen et al., 1991, Science 254: 1497). "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The term "basic" or "positively charged" amino acid as used herein, refers to amino acids in which the R groups have a net positive charge at pH 7.0, and include, but are not limited to, the standard amino acids lysine, arginine, and histidine.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "cancer" as used herein is defined as proliferation of cells whose unique trait—loss of normal controls—results in unregulated growth, lack of differentiation, local tissue invasion, and metastasis. Examples include but are not limited to, breast cancer, prostate cancer, ovarian cancer, cervical cancer, skin cancer, pancreatic cancer, colorectal cancer, renal cancer and lung cancer. The terms "cell," "cell line," and "cell culture" as used herein may be used interchangeably. All of these terms also include their progeny, which are any and all subsequent generations. It is understood that all progeny may not be identical due to deliberate or inadvertent mutations.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to a polypeptide, an isolated nucleic acid, or other agent used in the method of the invention.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "enhancing bone repair" as used herein refers to methods of speeding up or inducing better bone repair using compounds of the invention, relative to the speed or amount of bone repair that occurs without administration of compounds of the invention.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "enhancer" is a DNA regulatory element that can increase the efficiency of transcription, regardless of the distance or orientation of the enhancer relative to the start site of transcription.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound of the invention to reduce or impede a described function. Preferably, inhibition is by at least 10%, more preferably by at least 25%, even more preferably by at least 50%, and most preferably, the function is inhibited by at least 75%.

The phrase "inhibit cancer cell growth", as used herein, refers to both direct and indirect inhibition of growth, regardless of the mechanism. For example, inhibiting a cancer cell from adhering to another cell or substrate can inhibit growth indirectly, when adhesion is required for the cell to proliferate.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, *Antibodies, A Laboratory Manual*, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Osteogenesis" as used herein refers to bone growth, bone remodeling and repair of bone due to injury or disease.

As used herein, a "peptide" encompasses a sequence of 2 or more amino acid residues wherein the amino acids are naturally occurring or synthetic (non-naturally occurring) amino acids covalently linked by peptide bonds. No limitation is placed on the number of amino acid residues which can comprise a protein's or peptide's sequence. As used herein, the terms "peptide," "polypeptide," and "protein" are used interchangeably. Peptide mimetics include peptides having one or more of the following modifications:

1. peptides wherein one or more of the peptidyl —C(O) NR— linkages (bonds) have been replaced by a non-peptidyl linkage such as a —CH$_2$-carbamate linkage (—CH$_2$OC(O) NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl;

2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or C$_1$-C$_4$ alkyl with the proviso that R and R$_1$ are not both hydrogen;

3. peptides wherein the C terminus is derivatized to —C(O) R$_2$ where R$_2$ is selected from the group consisting of C$_1$-C$_4$ alkoxy, and —NR$_3$R$_4$ where R$_3$ and R$_4$ are independently selected from the group consisting of hydrogen and C$_1$-C$_4$ alkyl.

Synthetic or non-naturally occurring amino acids refer to amino acids which do not naturally occur in vivo but which, nevertheless, can be incorporated into the peptide structures described herein. The resulting "synthetic peptide" contains amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "polylinker" is a nucleic acid sequence that comprises a series of three or more different restriction endonuclease recognitions sequences closely spaced to one another (i.e. less than 10 nucleotides between each site).

A "polynucleotide" means a single strand or parallel and anti-parallel strands of a nucleic acid. Thus, a polynucleotide may be either a single-stranded or a double-stranded nucleic acid.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "non-native promoter" as used herein refers to any promoter that has been operably linked to a coding sequence wherein the coding sequence and the promoter are not naturally associated (i.e. a recombinant promoter/coding sequence construct).

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Plurality" means at least two.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "reversibly implantable" device is one which may be inserted (e.g. surgically or by insertion into a natural orifice of the animal) into the body of an animal and thereafter removed without great harm to the health of the animal.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds," as used herein, is meant an antibody or compound which recognizes and binds a molecule of interest (e.g., an antibody directed against a polypeptide of the invention), but does not substantially recognize or bind other molecules in a sample.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. As used herein, the term "treating" includes alleviating the symptoms associated with a specific disease, disorder or condition and/or preventing or eliminating said symptoms.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, plasmids, cosmids, lambda phage vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

A limited number of proteins have been identified as being primarily associated with bone tissue. In addition, reports in the literature have presented compelling evidence that the targets of these proteins are receptors on the cell surface. Without wishing to be bound by any particular theory, it is theorized that protein domains may be responsible for targeting these proteins to cell receptors or receptor ligands in the extracellular matrix of the target tissue. Therefore, these peptides could be used for a wide variety of therapeutic uses including the delivery of drugs that could help in the treatment of musculoskeletal disorders, genetic or acquired, osteoporosis, and metastatic cancer. Furthermore, it is anticipated that the peptides themselves can serve as therapeutic agents providing osteogenic or tropic activity for osteoblast, mesenchymal or hematopoietic cell lineages.

Applicants have previously identified numerous peptides that are bone targeting peptides and these peptides are used herein (see U.S. Pat. Pub. No. 2005/0085623 and the Examples of the present application).

The present invention is directed to the use of peptides that target bone and bone marrow, regulate cell adhesion, regulate angiogenesis, as well as methods for using biocompatible compositions comprising these peptides for treating disorders and diseases of these functions. The bone targeting peptides were identified using a phage display library based on their ability to bind and become localized to bone tissue after general injection into a mouse. Accordingly, one aspect of the present invention is directed to the use of purified peptides comprising the following sequences:

```
                                       (SEQ ID NO: 1) (L1)
THR-MET-ARG-ASN-PRO-ILE-THR-SER-LEU-ILE-SER-VAL-
GLY-GLY-GLY-SER, (SEQ ID NO: 2) (L2)
LEU-LEU-ALA-ASP-THR-THR-HIS-HIS-ARG-PRO-TRP-THR-
GLY-GLY-GLY-SER, (SEQ ID NO: 3) (L5)
LYS-GLU-ILE-PRO-PRO-ILE-PRO-LEU-LEU-ALA-PRO-SER-
GLY-GLY-GLY-SER, (SEQ ID NO: 4) (L6)
ASN-ASN-VAL-SER-GLN-LYS-TRP-GLN-GLN-ARG-LEU-ILE-
GLY-GLY-GLY-SER, (SEQ ID NO: 5) (L7)
ASN-SER-MET-ILE-ALA-HIS-ASN-LYS-THR-ARG-MET-HIS-
GLY-GLY-GLY-SER, (SEQ ID NO: 6) (L11)
GLY-ILE-HIS-VAL-PRO-TRP-MET-PRO-PRO-VAL-ALA-PHE-
GLY-GLY-GLY-SER, (SEQ ID NO: 7) (L12)
GLN-ARG-SER-TRP-THR-LEU-ASP-SER-ALA-LEU-SER-MET-
GLY-GLY-GLY-SER, (SEQ ID NO: 8) (L13)
SER-GLY-HIS-GLN-LEU-LEU-LEU-ASN-LYS-MET-PRO-ASN-
GLY-GLY-GLY-SER, (SEQ ID NO: 9) (L14)
SER-SER-THR-LEU-LYS-THR-PHE-PHE-GLY-PHE-PRO-ASP-
GLY-GLY-GLY-SER, (SEQ ID NO: 10) (L19)
ASP-SER-SER-ASN-PRO-ILE-PHE-TRP-ARG-PRO-SER-SER-
GLY-GLY-GLY-SER, (SEQ ID NO: 11) (R1)
ASN-TYR-SER-HIS-LEU-ARG-VAL-LYS-LEU-PRO-THR-PRO-
GLY-GLY-GLY-SER, (SEQ ID NO: 12) (R2)
SER-GLY-HIS-GLN-LEU-LEU-LEU-ASN-LYS-MET-PRO-ASN-
GLY-GLY-GLY-SER, (SEQ ID NO: 13) (R3)
ALA-THR-TRP-SER-HIS-HIS-LEU-SER-SER-ALA-GLY-LEU-
GLY-GLY-GLY-SER, (SEQ ID NO: 14) (R8)
SER-TYR-SER-GLN-MET-ASP-PRO-PRO-ARG-SER-LEU-PRO-
GLY-GLY-GLY-SER, (SEQ ID NO: 15)
THR-MET-ARG-ASN-PRO-ILE-THR-SER-LEU-ILE-SER-VAL, (SEQ ID NO: 16)
LEU-LEU-ALA-ASP-THR-THR-HIS-HIS-ARG-PRO-TRP-THR, (SEQ ID NO: 17)
LYS-GLU-ILE-PRO-PRO-ILE-PRO-LEU-LEU-ALA-PRO-SER, (SEQ ID NO: 18)
ASN-ASN-VAL-SER-GLN-LYS-TRP-GLN-GLN-ARG-LEU-ILE, (SEQ ID NO: 19)
ASN-SER-MET-ILE-ALA-HIS-ASN-LYS-THR-ARG-MET-HIS, (SEQ ID NO: 20)
GLY-ILE-HIS-VAL-PRO-TRP-MET-PRO-PRO-VAL-ALA-PHE, (SEQ ID NO: 21)
GLN-ARG-SER-TRP-THR-LEU-ASP-SER-ALA-LEU-SER-MET, (SEQ ID NO: 22)
SER-GLY-HIS-GLN-LEU-LEU-LEU-ASN-LYS-MET-PRO-ASN, (SEQ ID NO: 23)
SER-SER-THR-LEU-LYS-THR-PHE-PHE-GLY-PHE-PRO-ASP, (SEQ ID NO: 24)
ASP-SER-SER-ASN-PRO-ILE-PHE-TRP-ARG-PRO-SER-SER, (SEQ ID NO: 25)
ASN-TYR-SER-HIS-LEU-ARG-VAL-LYS-LEU-PRO-THR-PRO, (SEQ ID NO: 26)
SER-GLY-HIS-GLN-LEU-LEU-LEU-ASN-LYS-MET-PRO-ASN,
```

-continued (SEQ ID NO: 27)
ALA-THR-TRP-SER-HIS-HIS-LEU-SER-SER-ALA-GLY-LEU, (SEQ ID NO: 28)
SER-TYR-SER-GLN-MET-ASP-PRO-PRO-ARG-SER-LEU-PRO, (SEQ ID NO: 29) (D1P1)
LEU-PRO-TRP-THR-GLU-PRO-SER-PHE-TRP-ARG-THR-PRO-
GLY-GLY-GLY-SER,
and (SEQ ID NO: 30)
LEU-PRO-TRP-THR-GLU-PRO-SER-PHE-TRP-ARG-THR-PRO, as well as bioactive homologs, fragments, and derivatives of SEQ ID NOs: 1-30 that exhibit bone targeting properties. Homologs and derivatives of SEQ ID NOs: 1-30 include amino acid sequences that differ from those sequences either by one or more conservative amino acid substitutions, or by one amino acid deletion, addition, or substitution. In one embodiment, the peptides comprise a sequence identical to SEQ ID NO: 1-30, or differ from SEQ ID NO: 1-30 by 1-2 conservative amino acids.

In accordance with one embodiment, the use of a peptide is provided having a maximum length of 25 amino acids and comprising an amino acid sequence selected from the group consisting of SEQ ID NOs: 1-30. In one embodiment, the bone targeting protein consists of an amino acid sequence selected from the group consisting of SEQ ID NO: 1-30.

The peptides can be prepared from natural proteins, produced recombinantly or more preferably they are chemically synthesized using techniques well know to those skilled in the art.

The present invention is also directed to antibodies that specifically bind to a peptide selected from the group consisting of SEQ ID NOs:1-30.

The present invention is also directed to isolated nucleic acids comprising nucleic acid sequences which encode peptides of the invention, and homologs, fragments and derivatives thereof. In one aspect, the peptides comprise sequences selected from the group of sequences consisting of SEQ ID NOs:1-30.

In one embodiment, the peptides of the invention inhibit cell adhesion. In one aspect, the cell is an epithelial cell. In another aspect, the cell is an endothelial cell. In one aspect, the cell is a cancer cell. In one aspect, the cancer is an epithelial cancer. In another aspect, the cancer is prostate cancer. Various adhesion assays are known to those of ordinary skill in the art.

In one embodiment, the peptides of the invention inhibit metastasis. In one aspect, the peptides of the invention inhibit metastasis by inhibiting adhesion of cancer cells.

In one embodiment, the peptides of the invention are useful for regulating osteogenesis. In one aspect, the peptides of the invention are useful for enhancing repair of bone defects or injuries. In one aspect, the peptides included L1, L6, L7, and L12 (SEQ ID NOs:1, 4, 5, and 7, respectively).

In one embodiment, the peptides of the invention can be administered with a biocompatible material to help induce and enhance bone repair. In one aspect, the biocompatible material is gelfoam. In one aspect, peptide and biocompatible material are delivered directly to site of bone injury.

In one aspect, an isolated nucleic acid comprising a nucleic acid sequence encoding a peptide of the invention can be administered to a subject.

In one embodiment, the peptides of the invention bind to a cell. In one aspect, the cell is selected from the group consisting of bone cells, endothelial cells, epithelial cells, and bone marrow cells. In one aspect, the bone marrow cells are mesenchymal cells.

In one embodiment, peptides of the invention bind with nucleolin. In one aspect, the peptide is L13 (SEQ ID NO:8).

In one embodiment, the peptides of the invention bind with vimentin. In one aspect, the peptides are L12 and R8. (SEQ ID NOs:7 and 14, respectively).

In one embodiment, the bone targeting peptides of the invention are useful for identifying proteins which bind with the bone targeting peptides. In one aspect, the proteins are associated with the cell surface. In another aspect, the proteins are intracellular.

In one embodiment, the peptides of the invention comprise carboxy termini linker sequences, wherein said linker has four amino acid residues, the first three residues of which are glycine and the fourth of which is serine. In one aspect, the peptides have a sequence selected from the group consisting of SEQ ID NOs:1-14 and 29, and homologs, derivatives and fragments thereof.

In one embodiment, the peptides of the invention do not comprise carboxy termini linker sequences. In one aspect, the peptides have a sequence selected from the group consisting of SEQ ID NOs:15-28 and 30, and homologs, derivatives, and fragments thereof.

The present invention also encompasses pharmaceutical and therapeutic compositions comprising the bone targeting peptides of the present invention.

Non-synthetic matrix proteins like collagen, glycosaminoglycans, and hyaluronic acid, which are enzymatically digested in the body, have also been used to deliver bioactive proteins to bone areas (see U.S. Pat. Nos. 4,394,320; 4,472,840; 5,366,509; 5,606,019; 5,645,591; and 5,683,459) and are suitable for use with the present invention. The bone targeting peptide compositions can be further combined with a demineralized bone material, growth factor, nutrient factor, pharmaceutical, calcium-containing compound, anti-inflammatory agent, antimicrobial agent, or any other substance capable of expediting or facilitating bone growth. Examples of osteoinductive factor suitable for use with the compositions of the present invention include demineralized bone particles, a Bone Morphogenetic Protein, an osteoinductive extract of demineralized bone matrix, or a combination thereof.

Examples of growth factors suitable for use with the composition of the present invention include Transforming Growth Factor-Beta (TGF-β), Transforming Growth Factor-Alpha (TGF-α), Epidermal Growth Factor (EGF), Insulin Like Growth Factor-I or II, Interleukin-I (IL-I), Interferon, Tumor Necrosis Factor, Fibroblast Growth Factor (FGF), Platelet Derived Growth Factor (PDGF), and Nerve Growth Factor (NGF).

The compositions of the present invention can also be combined with inorganic fillers or particles. For example for use in implantable grafts the inorganic fillers or particles can be selected from hydroxyapatite, ti-calcium phosphate, ceramic glass, amorphous calcium phosphate, porous ceramic particles or powders, mesh titanium or titanium alloy, or particulate titanium or titanium alloy.

In accordance with one embodiment of the invention, a method is provided for regulating tumor growth, angiogenesis, cell adhesion and osteogenesis, as well as diseases and disorders thereof.

In one embodiment, the method comprises the steps of administering a peptide selected from the group consisting of SEQ ID NOs:1-30 to a patient in need thereof. In one embodiment a composition comprising these peptides is administered locally by injection. Compositions comprising the peptides of SEQ ID NOs:1-30 can be further combined with other known drugs, and in one embodiment the drugs are covalently bound to the peptides. These compositions can be prepared in the form of an implantable device that can be molded to a desired shape. In one embodiment a graft construct is prepared comprising a biocompatible matrix and one or more of the bone targeting peptides of the present invention, wherein the matrix is formed in a shape to fill a gap or space created by the removal of a tumor or diseased tissue.

In accordance with one embodiment, the bone targeting peptides of the present invention are complexed or linked to one or more bioactive agents. The bioactive agents can be linked to the bone targeting peptides through hydrogen, ionic, or covalent bonding. In one preferred embodiment the bioactive agent is covalently linked to the bone targeting peptides of the present invention. Also in accordance with this invention is the use of indirect means for associating the bioactive agents with the peptides including by connection through intermediary linkers, spacer arms, bridging molecules, or liposome entrapment. In one embodiment the peptide/bioactive agent complex can be used to deliver therapeutic pharmaceuticals to bone or cartilage tissues, wherein the bioactive agents are encapsulated within the liposome. Bioactive agents suitable for use with the present invention include antibodies, growth factors, toxins (such as aflatoxin, digoxin, xanthotoxin, and rubratoxin), antibacterial agents (such as cephalosporins, penicillin, erythromycin, ciprofloxacin, cinoxacin, and norfloxacin), cancer drugs (including chemotherapeutic agents) and nucleic acids. In one embodiment the bone targeting protein is linked to a chemotherapeutic agent or other cancer drug and the complex is used to treat a patient suffering from cancer, especially bone cancer or cancer that has metastasized to bone or cartilaginous tissues.

In another embodiment of the present invention a method is provided for identifying and isolating the putative receptors for the bone targeting peptide sequences. The method comprises identifying the putative receptors by affinity chromatography and by two-dimensional peptide mapping of cell membrane proteins and extracellular matrix molecules. More particularly, the peptides of SEQ ID NOs: 1-24 will be immobilized on a solid support and the peptides will then be contacted with cell membrane proteins and extracellular matrix molecules to identify molecules that specifically bind to the bone targeting peptides.

The bone targeting peptides can be used in a variety of therapeutic applications. For example, for those individual peptides that are found to bind specifically to cells or extracellular matrix in bone, their potential as carriers of pharmacologic agents, such as polypeptide factors and therapeutic genes, can be explored.

There are several other implications to the discovery that peptides target bone and bone marrow, as well as regulate angiogenesis, cell adhesion, and osteogenesis, particularly if the peptides are merely targeting bone matrix or cells without having a direct effect on metabolic properties at their destinations. These characteristics can then be exploited by coupling drugs, such as growth factors, or genes to the tropic peptides, as a means of targeting pharmaceuticals to specific destinations in the skeleton, thereby raising a number of possibilities for therapeutic intervention for cancer metastases as well as for skeletal repair and regeneration.

One aspect of the present invention relates to osteogenic devices, and more specifically to synthetic implants which induce osteogenesis in vivo in mammals, including humans. More particularly, this embodiment of the invention relates to biocompatible, bioresorbable, synthetic compositions comprising the bone targeting proteins disclosed herein. These compositions are anticipated to have osteogenic properties and/or are tropic for osteogenic cell lineages. The implants can be prepared using previously described implant materials such as hydroxlapatite, autogenous bone grafts, allogenic bone matrix, demineralized bone powder, and collagenous matrix. The bone targeting peptides of the present invention can be combined with known graft materials that are fully formable at temperatures above 38° C. but become a solid at temperatures below 38° C. Such compositions as Opteform 100HT (University of Florida Tissue Bank) comprise a thermoplastic human derived inert carrier allowing the material to stay rigid once it reaches body temperature. In another embodiment, the bone targeting peptides are combined with known materials to provide a composition for coating implantable prosthetic devices, and to increase the cellular ingrowth into such devices.

In one aspect of the invention the matrix material is provided as a coating on an implant placed in contact with viable bone. Useful implants are composed of an inert material such as ceramic, glass, metal, or polymer. In another aspect of the invention, bone growth is induced from a viable mammalian bone by contacting the bone with matrix material comprising a bone targeting peptide, into which has been dispersed a glue in an amount sufficient to solidify the matrix when implanted in a mammal or when placed at 37° C. One glue suitable for such use is methyl cellulose. The matrix solidifies substantially in the shape of the implanted matrix.

One of ordinary skill in the art would appreciate that there are other carriers useful for delivering the peptides of the invention. Such carriers include, but are not limited to, calcium phosphate, hydroxyapatite, and synthetic or natural polymers such as collagen or collagen fragments in soluble or aggregated forms. In one aspect, such carriers serve to deliver the peptides to a location or to several locations. In another aspect, the carriers and peptides can be delivered either through systemic administration or by implantation. Implantation can be into one site or into several sites. Use of the carriers to help deliver the peptides to induce a biological effect must not negate the biological activity of the peptide, either in vivo or in vitro.

In one embodiment, the peptides of the invention may be further incorporated into a fusion protein. Said fusion protein may comprise a peptide of the invention, or homologs, fragments, or derivatives thereof. Said fusion protein may be covalently attached to collagen or to collagen fragments or to derivatives of collagen, or to natural or synthetic polymers that are biodegradable or non-biodegradable. In one aspect, such carriers serve to deliver the peptides to a location or to several locations. In another aspect, the fusion protein comprising a peptide of the invention can be delivered either through systemic administration or by implantation. Implantation can be into one site or into several sites. Use of the fusion protein to help deliver the peptides to induce a biological effect must not negate the biological activity of the peptide, either in vivo or in vitro.

It will be appreciated, of course, that the peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The peptides of the present invention may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

The invention is also directed to methods of administering the compounds of the invention to a subject. In one embodiment, the invention provides a method of treating a subject by administering compounds identified using the methods of the invention description. Pharmaceutical compositions comprising the present compounds are administered to an individual in need thereof by any number of routes including, but not limited to, topical, oral, intravenous, intramuscular, intraarterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at compound of the present invention to a patient in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Example 1

Binding of Peptides to Cells

Methods: Four-week old Swiss Webster mice were euthanized; the femurs were excised and decalcified in 0.25M EDTA in PBS solution for 5 days, and washed in PBS for 24 hours. The femoral shafts were obtained by cutting off the proximal and distal ends of the femur. The femoral shafts were placed in Tissue-Tek O.C.T. Compound (Sukura Finetek, Torrance, Calif.) and frozen at −20° C. overnight. Sections were cut at 10 µm serially with a cryomicrotome, rinsed with 1% BSA in PBS three times. To block nonspecific reaction sections were incubated with Avidin/Biotin Blocking Kit (Vector Laboratories, Inc. Burlingame, Calif.) according to the manufacturer's instructions. Following another rinse with PBS, 150 µl 10 mM solution of each biotinylated peptide (L1, L2, L7, R1, R8) was added to the slides and incubated for 1 hour at room temperature. In negative controls, only PBS was added. After rewashes with 1% BSA, 150 µl of 1:50,000 dilution of Avidin-FITC was added to each slide and incubated overnight at 4° C.

The sections were washed with 1% BSA in PBS and mounted with Vectashield (Vector Laboratories Inc., Burlingame, Calif.). Fluorescence was visualized using a Nikon eclipse E600 microscope (Nikon, Melville, N.Y.) equipped with a 535 nm wavelength fluorescein filter. Images were obtained using a Sony DKC-5000 digital camera (Sony Electronics Inc.) and processed with Adobe Photoshop software (Adobe Systems Incorporated, San Jose, Calif.).

Peptides: Preparation of the peptides was performed as described in U.S. Pat. Pub. No. 2005/0085623 (Balian et al., published Apr. 21, 2005), which is incorporated by reference in its entirety herein, and as described below.

Results: Fluorescence was detected in sections incubated with peptides L1, L2, L7, and R1. The distribution of fluorescence throughout the marrow was uneven. In sections incubated with L7, most of the cells were detectable but fluorescence intensity was variable. Cells that appeared morphologically elongated showed the highest fluorescence intensity. The round cells showed less intensity of fluorescence and some of them were not detectable. Incubation of sections with L1, L2, R1, and R8 did not detect as many cells, and peptides L1, R1, and R8 recognized the round cells preferentially, while L2 recognized cells with mostly irregular shapes. In control slides incubated with PBS without peptide, none of the cells could be detected by fluorescence (FIG. 1).

Summary: Without wishing to be bound by any particular theory, the results suggest that binding of the bone tropic peptides that were obtained from the phage display library bind to bone is cell type specific, indicating that the peptides with different sequences are likely to have varying biological activities on bone.

Example 2

Regulation of Adhesion of Endothelial Cells

Peptides from the phage display project were added to bovine aortic endothelial cells in culture. The endothelial cells had adhered to a surface coated with collagen or with fibronectin. Addition of the peptide had an effect an these cells within one hour.

The effect of some of the peptides was to detach the cells completely from the substratum; in some instances all of the cells were completely detached, while other peptides had no effect whatsoever on the cells, that resembled the cells in the controls (treated with PBS). A third group of peptides affected a few of the cells, by binding to them (detected by biotin avidin staining) causing the cells to become spherical. The experiments suggest that some peptides are capable of reversing or inhibiting the adhesion of cells to a substratum consisting of extracellular matrix components, thus preventing angiogenesis.

Methods

Experiment 1: Bovine aortic endothelial cells were plated on glass slides that were coated either fibronectin or collagen. The cell density was 5,000 cells/well. After the cells adhered for four hours, 0.1M of biotinylated peptide was added to each well. The following peptides were used: L1, L2, L5, L6, L7, L12, L13, L14, L19, R1, R3, and R8.

To perform this experiment, the media was removed and the cells were rinsed with 1×PBS plus 1% BSA three times. Peptides were diluted in 1×PBS plus 1% BSA, added to cells and incubated for 1 hour. The cells were rinsed three times with 1% BSA in PBS, and fixed with 2% parafomaldehyde. Aldehyde groups were blocked with 0.2 M HCl-glycine in PBS, the cells were rinsed three times with 1% BSA in PBS and ExtrAvidin-FITC (1:200 dilution) was added and incubated overnight at 4° C. The cells were rinsed three times with 1% BSA in PBS. The chambers and the gasket were removed from each slide, Vectashield was added, covered and viewed on a Nikon microscope. Images were acquired using a Coolsnap digital camera and Metavue software.

Experiment 1 Results (FIG. 2) Peptide staining could be divided into 3 main groups. In the first group, the cells lifted and formed clusters that stained intensely (L1, L7, L12) (SEQ ID NOs:1, 5, and 7, respectively). In the second group, there was no effect, with results similar to PBS (D1P1, L2, L14, L13, L19) (SEQ ID NOs:29, 2, 9, 8, and 10, respectively). In the third group, the cells had lifted completely and most of the cells disappeared from the surface of the slides, leaving a lot of cell debris (L5, L6, R1 and R3) (SEQ ID NOs:3, 4, 11, and 13, respectively).

The sequence for D1P1, with and without the four amino acid residue linker, is:

LEU-PRO-TRP-THR-GLU-PRO-SER-PHE-TRP-ARG-THR-PRO-GLY-GLY-GLY-SER (SEQ ID NO:29), and

LEU-PRO-TRP-THR-GLU-PRO-SER-PHE-TRP-ARG-THR-PRO (SEQ ID NO:30).

The DIP1 peptide was prepared based on the sequence of phage obtained from biopanning experiments on D1 (marrow mesenchymal-osteoprogenitor) cells in vitro, and was used in this experiment with the linker (SEQ ID NO:29).

Experiment 2: Bovine aortic endothelial cells (BAEC) were plated as in experiment 1. In this experiment, however, the cells had been attached for 48 hours (instead of 4 hours as in experiment 1) before the addition of peptides. Nevertheless, the results were identical to those described in experiment 1 above where peptide was added on day 0 after the cells adhered.

Experiment 3: The cells were adherent for about 6 hours and peptides at various concentrations were added to the cells. The concentrations of each of the peptides used in this experiment were: 0.1M, 0.01M, 0.001M and 0.0001M biotinylated peptide. The following peptides were tested: L1, L5, L6, L7, L13, L14, R1, R3, R8, DIP1 and PBS control (SEQ ID NOs:1, 3, 4, 5, 8, 9, 11, 13, 14, and 29).

Experiment 3 Results: Treatment with 0.1M peptide showed the same effect on the cells as in experiments 1 and 2 above; the one exception was the cells treated with L12, which formed fewer clumps and considerably more debris. The peptides at 0.01M, which is one tenth of the concentration used in experiments 1 and 2, were ten times less effective at detaching and clumping the cells and on the generation of cell debris.

Example 3

Osteogenesis Mediated by Bone Targeting Peptides

Figure 3A:
FIG. 3a, comprising six micrographs (3aA-3aF), is a representation of micrographs demonstrating the effects of the peptide L7 on osteogenesis in gelfoam at two weeks. The upper panels (3aA and 3aB) are gelfoam controls only (photographed at 4× (left panel) and at 10× (right panel) magnification. The middle panels (C and D) represent the effects of 20 mM L7 and the lower panels (E and F) represent the effects of 100 mM L7.
Figure 3A:
Figure 3A:
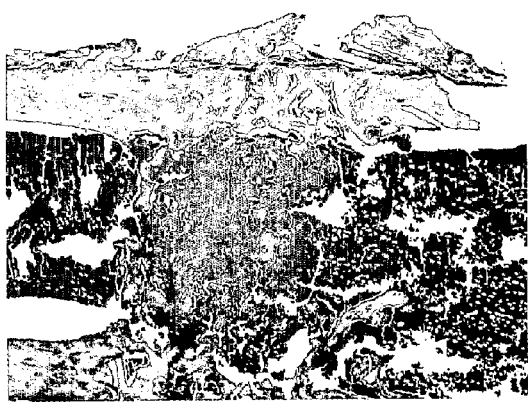
Figure 3A:
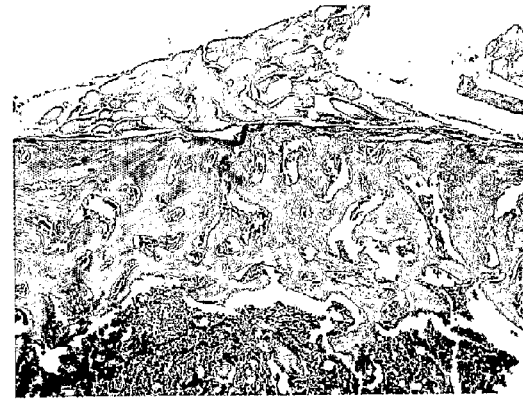
Figure 3A:
Figure 3A:
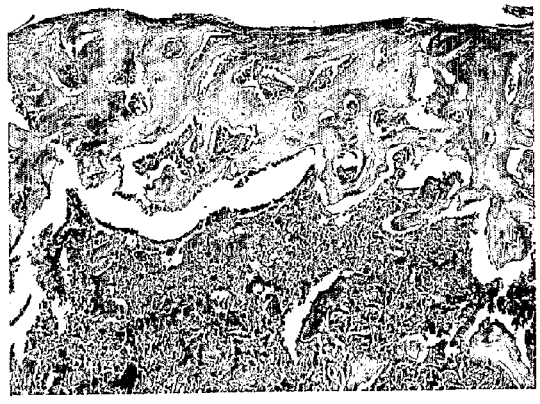
Figure 3B:
FIG. 3b, comprising six micrographs (3bA-3bF), is a representation of micrographs demonstrating the effects of the peptide L12 on osteogenesis in gelfoam at two weeks. The upper panels (3bA and 3bB) are gelfoam controls only (photographed at 4× (left panel) and at 10× (right panel) magnification. The middle panels (C and D) represent the effects of 20 mM L12 and the lower panels (E and F) represent the effects of 100 mM L12.
Figure 3B:
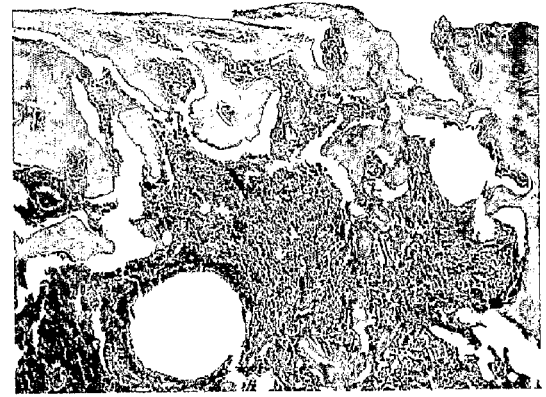
Figure 3B:
Figure 3B:
Figure 3B:
Figure 3B:
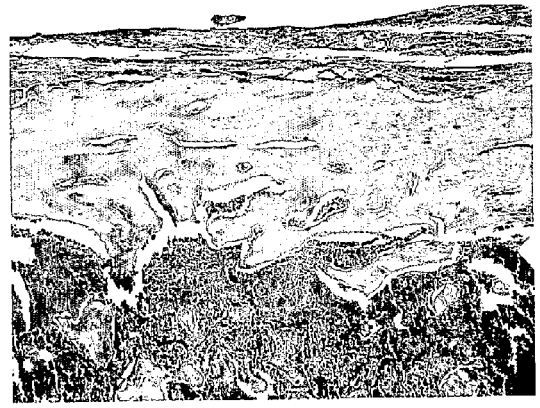
Figure 4A:
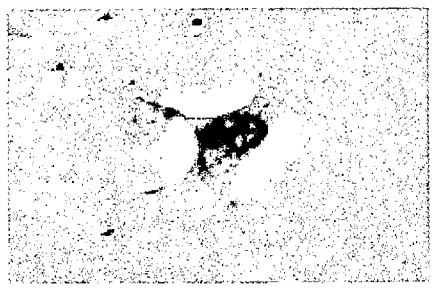
FIG. 4, comprising FIGS. 4A (phase contrast micrograph; L13), 4B (fluorescence micrograph; L 3), 4C (phase contrast micrograph; R1), and 3D (fluorescence micrograph; R1), represents micrographic images of D1 bone marrow mesenchymal cells incubated with the peptides L13 (SEQ ID NO: 8) or R1 (SEQ ID NO:11).
Figure 4B:
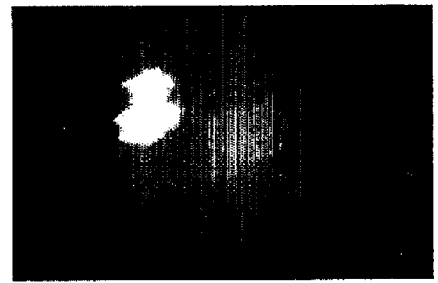
Figure 4C:
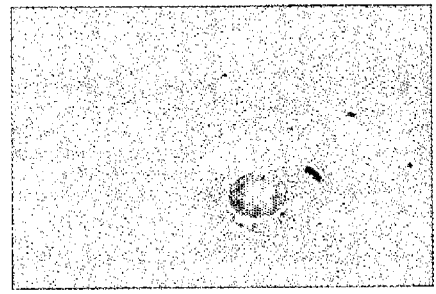
Figure 4D:

FIGS. 3a & 3b

Methods
Preparation of Gelfoam-Peptide Composite

Gelfoam cylinders were created. A 1.5 mm diameter and 10 mm long piece of gelfoam was made using a self-designed instrument 24 hours before surgery, and the gelfoam cylinders was put into 20 mM or 100 mM peptide solution (L1, L6, L7 and L12; SEQ ID NOs:1, 4, 5, and 7, respectively) in PBS or for the control experiment, in PBS that did not contain peptide. The gelfoam cylinders were transferred into 12 well culture dishes, sterilized by exposure to ultraviolet light and stored overnight at −20° C. At the time of surgery, the gelfoam-peptide composites were manipulated on ice, cut transversely using a surgical scalpel and divided into equal parts 2 mm in length.

Surgical Procedure

The Institutional Animal Care and Use Committee approved the surgical procedure prior to surgery. After intraperitoneal anesthesia with a mixture of ketamine (50 grams/gram body weight) and xylazine (5 grams/gram body weight), a 1.5 mm diameter critical-sized unicortical defect was made in the front aspect of each femur, the defect was located 5 mm above the condyle in 6 adult Fischer 344 rats, using a 1.5 mm hand drill through a lateral incision. The same size defect was also created in the anteromedial aspect of tibias.

The femurs and tibias were randomly divided into 6 groups: no repair (empty), gelfoam only, L7 100 mM (L6 100 mM in tibia)+gelfoam, L7 20 mM (L6 20 mM in tibia)+gelfoam, and L12 100 mM (L1 100 mM in tibia)+gelfoam, L12 20 mM (L1 20 mM in tibia)+gelfoam group, each group consisted of 2 femurs or two tibias.

The 2 mm gelfoam-peptide or gelfoam without peptide composites were implanted into the femoral defects except for the empty control group. Full weight bearing was permitted immediately after surgery.

Methods of Analysis

One animal was used to evaluate the femurs and tibia from each group for gross and histological evaluation at 2 and 4 weeks post-surgery. After checking the bone defect carefully, the harvested femora were fixed in 10% neutral buffered formalin, decalcified in RDO rapid decalcifier for 14 hours, embedded in paraffin and processed for routine histology. Serial 10 μM sections were made on a microtome and then stained with hematoxylin/eosin (HE). Bone regeneration was evaluated by gross and light microscopic examination.

Results

Gross Examination:

At 2 weeks, the repair tissue surface was more elevated in all the groups with gelfoam-peptide composite. The border between newly formed tissue and normal bone was no longer well defined. The defects that received gelfoam (without peptide) were entirely filled but did not show a surface that was elevated above that of the adjacent bone surface. The color of newly formed tissue was somewhat darker than normal bone. In the control group, however, the repair tissue did not fill the defect completely, and the surface depressed compared with the surface of bone adjacent to the defect. At 4 weeks, the bone defect was hardly visible in all of the groups and no obvious difference was found between groups treated with gelfoam with or without peptide.

Histologic Examination

At 2 weeks, repair tissue filled the defects in both groups treated with gelfoam and with gelfoam-peptide composites. However, the amount of cortical bone and bone within the medullary canal of repair tissue in the group treated with gelfoam-peptide was larger than in the group treated with gelfoam and no peptide. The density, thickness and cortical continuity of repair tissue with gelfoam-peptide composites were greater, especially in the specimens that received peptides at a concentration of 100 mM group. The repair tissue in specimens that were not treated with gelfoam did not completely fill the bone defect (FIGS. 3a and 3b).

Example 4

Peptide Binding

Selection of a phage display 12-mer peptide library was based on the likelihood that antibodies can be raised to the selected peptides, and that the combination of the peptides and their antibodies can provide a useful tool to confirm specificity of peptide-ligand binding. If a given peptide binds to the cell surface, the antibodies are likely to serve as a tool to further examine the effects of peptides on cell bioactivity. It was hypothesized that from a random phage display peptide library of $2.7 \times 10^9$ different peptide sequences, unique peptide sequences could be retrieved that interact specifically with cellular components of bone. This is essentially biopanning in vivo. It was found that when these phages were reintroduced into mice, at least some of the bone targeting peptides are retrievable from bone, that is, peptides were obtained in bone and did not reappear elsewhere in significant amounts, based on plaque forming units, in other tissues that were examined such as liver and kidney.

In vivo biopanning with a random 12-mer peptide phage display library and DNA sequencing were performed, resulting in the isolation and identification of 13 peptide sequences enriched selectively from their interaction with bone (L13 and R2 having the same sequence). The final 13 peptide sequences were detected repeatedly in phage that was isolated from bone and bone marrow.

The studies disclosed herein have shown that some of the bone targeting peptides, such as R1 and L7 (SEQ ID NOs:11 and 5, respectively) (see examples), potentiate bone regeneration in vivo.

TABLE 1

Selected sequences and their frequency

| PEPTIDE NAME | PHAGE SEQUENCE FREQUENCY* | PERCENT FREQUENCY |
|---|---|---|
| L14 | 12/30 | 40.0 |
| R3 | 10/29 | 34.5 |
| L2 | 9/28 | 32.1 |
| L1 | 8/28 | 28.6 |
| R1 | 7/29 | 24.1 |
| R8 | 7/29 | 24.1 |
| L13 | 7/30 | 23.3 |
| L6 | 5/28 | 17.9 |
| L5 | 5/28 | 17.9 |
| L12 | 5/30 | 16.7 |
| L19 | 5/30 | 16.7 |
| L7 | 1/28 | 3.6 |
| L11 | 1/30 | 3.3 |

*Phage frequency: number of times the sequence was found in a group of plaques.

Peptide Synthesis

Phage display describes a selection technique in which a peptide or protein is expressed as a fusion with a coat protein of a bacteriophage, resulting in display of the fused protein on the surface of the virion, while the DNA encoding the fusion resides within the virion. Phage display has been used to create a physical linkage between a vast library of random peptide sequences to the DNA encoding each sequence, allowing rapid identification of peptide ligands for a variety of target molecules (antibodies, enzymes, cell-surface receptors, etc.) by an in vitro selection process called biopanning. Biopanning is carried out by incubating a library of phage-displayed peptides with cells in vitro, washing away the unbound phage and eluting the specifically-bound phage. The eluted phage is then amplified and taken through additional binding/amplification cycles to enrich the pool in favor of binding sequences. After 3-4 rounds, individual clones are characterized by DNA sequencing. The biopanning can also be performed in vivo.

The Ph.D.-12 Phage Display Peptide Library Kit (New England Biolabs, Beverly, Mass.) used in this study is based on a combinatorial library of random peptide 12-mers fused to a minor coat protein (pIII). The displayed peptide 12-mers are expressed at the N-terminus of pIII, i.e., the first residue of the mature protein is the first randomized position. The peptide is followed by a short spacer of four amino acid residues, the first three residues of which are glycine and the fourth of which is serine, and then the wild-type III sequence. The library consists of approximately $2.7 \times 10^9$ electroporated sequences, amplified once to yield approximately 55 copies of each sequence.

For in vivo biopanning, BALB/c mice 8 weeks of age were injected $3.4 \times 10^{10}$ pfu of phage into the heart. The animals were euthanized after 5 minutes, and the tissues (bone, bone marrow, kidney, liver, and spleen) were collected for analysis. The bound phage was eluted according the manufacturer's instructions. The eluted phage was titered, amplified, purified, and injected again at the same concentration. The procedure was repeated 4 times, yielding bone and bone marrow-homing phage clones with the frequencies listed in Table 1.

The frequency of each peptide in bone and bone marrow was compared with its location in other tissues such as liver, kidney, lung, spleen, and brain. Thirteen unique peptide sequences eluted from bone and marrow were identified were identified by sequencing phage DNA. The peptides were synthesized using the polystyrene solid support on a Protein Technologies Symphony Multiple Channel Synthesizer.

Example 5

Peptides Binding to Bone and Bone Marrow Cells

For localization of peptide binding to cells and tissue sections, biotinylated peptides were synthesized. Fluorescein-isothiocyanate (FITC) labeled Avidin was used to localize the peptides on cells in culture and in tissue sections in vitro by epiluminescence microscopy. In addition, the biotinylated peptides were detected at concentrations as low as 1 μM in slot blots.

Peptide Binding to Bone Tissue:

Cryosections of decalcified femurs harvested from 4 week BALB/c mice were incubated with biotinylated peptide and Avidin-FITC. Fluorescence was detected in sections incubated with peptides L1, L2, L7, and R1 (SEQ ID NOs:1, 2, 5 and 11, respectively). The distribution of fluorescence throughout the marrow was uneven. In sections incubated with L7 (SEQ ID NO:5), most of the cells were detectable but fluorescence intensity was variable. Cells that appeared morphologically elongated showed the highest fluorescence intensity. The round cells showed less fluorescence and some cells were not detectable by fluorescence. Incubation of sections with L1, L2, R1, and R8 (SEQ ID NOs:1, 2, 11, and 14, respectively) did not detect as many cells, and peptides L1, R1, and R8 recognized the round cells preferentially, while L2 recognized cells with mostly irregular shapes. In control slides incubated with PBS without peptide, none of the cells could be detected by fluorescence (not shown).

Peptide Binding to Cells Isolated from Bone Marrow

TABLE 2

Localization of peptide binding to cells and tissue

| | Cell type | | | |
|---|---|---|---|---|
| Peptide | HBME | BAEC | Marrow (cells in culture) | Bone/Marrow (tissue sections) |
| L7 | | ✓ | | ✓ |
| L12 | | ✓ | ✓ | |
| L13 | ✓ | - | ✓ | ✓ |
| R1 | | ✓ | ✓ | ✓ |
| R8 | ✓ | ✓ | ✓ | ✓ |

Check marks indicate positive binding observed with FITC, blank spaces indicate that data is not available, while a dash indicates a negative result.

Bone marrow cells isolated from mouse femur were lifted with ethylenediaminetetraacetic acid (EDTA) and trypsin, resuspended, and allowed to attach on fibronectin-coated chamber slides for Avidin-FITC staining. The results showed that some adherent cells from bone marrow blowouts showed detectable binding for L13, R1, and R8. The images in FIG. 4 show that peptides L13 and R1 bind to D1 cells. The D1 cell is a multipotential mesenchymal stem-like line that was isolated from bone marrow and shown to have the characteristics of osteoprogenitor cells. This cell line has been well established and used successfully in several in vitro and in vivo studies in our laboratory. Peptide binding to human bone marrow endothelial cells (HBME) and bovine aortic endothelial cells (BAEC) in culture was also tested using the same procedure. Table 2 shows the results of peptide binding to cells in culture and to tissue sections.

Example 6

Peptide Receptors (Binding Partners) on Cells Identified by Affinity Chromatography

TABLE 3

Identification of binding partners by affinity chromatography

| Peptide | Cell type | |
|---|---|---|
| | HBME | BAEC |
| L7 | – | – |
| L12 | – | ✓Vimentin |
| L13 | ✓Nucleolin | – |
| R8 | | ✓Vimentin |

Blank spaces indicate that data is not available, while a dash indicates a negative result.

Membrane and cytosol fractions from human bone marrow endothelial cells and bovine aortic endothelial cells were prepared and used to identify the components from within these fractions that bind to the peptides using affinity chromatography). The results showed that nucleolin was the major component that binds to peptide L13 (SEQ ID NO:8). Nucleolin binding was demonstrated consistently with lysates from HBME cells but not with lysates of BAEC. Cell surface nucleolin is present at higher concentrations in actively dividing cells and is down regulated in cells when they become quiescent. Nucleolin is the apparent cell surface receptor of E-coli intimin-gamma. Cell bound intimin has been proposed to trigger a host cell response similar to the extension of filipodia when cells bind to laminin. Although nucleolin is not bone specific, the experiments demonstrate the ability to perform affinity chromatography utilizing biotinylated phage display library peptides that are immobilized on avidin-agarose. In the lysates of BAEC, vimentin was found to bind to peptides R8 (SEQ ID NO:14) and L12 (SEQ ID NO:7). Vimentin being an intracellular protein, a component of the cytoskeleton, suggests that the peptides are small enough to enter the cells of the endothelium to bind their targets. Table 3 provides a summary of peptide-binding partners (putative receptors) identified by affinity chromatography of cell lysates.

Example 7

Gene Expression Analysis of Bone Marrow Derived Mesenchymal Stem Cells Treated with Peptides

TABLE 4

Microarray data for L13 (SEQ ID NO: 8) peptide

| Gene | Fold Change |
|---|---|
| Neural cell adhesion molecule 2 | +6.96 |
| Eph receptor A5 | +4.92 |
| Hypothetical protein MGC28705 | +4.59 |
| Ameloblastin | +3.73 |
| Procollagen, type I, alpha 1 | +3.03 |
| RIKEN cDNA 2410129E14 gene | +3.03 |
| Syndecan 4 | +3.03 |
| v-raf-1 leukemia viral oncogene 1 | +2.46 |
| Cartilage link protein 1 | +2.00 |
| Thyroid hormone receptor alpha | −1.23 |
| Cadherin 11 | −1.41 |
| Cadherin 11 | −1.62 |
| Fibronectin 1 | −2.64 |

Peptides at concentrations of 5, 10, 50, and 100 μM were added to bone marrow mesenchymal stem cells in culture. The cells were examined microscopically during the next several days to determine the effect of peptides on cell adhesion and cell proliferation. The cells treated with peptides did not show signs of detachment indicating that the 13 peptides did not have toxic effects on the cells. There was no inhibitory effect on cell adhesion by mesenchymal cells in the tissue culture system used.

For gene analysis, the bone marrow derived mesenchymal stem cells were seeded at 95,000 cells per well in a 6 well plate and maintained in culture media containing 100 μM/ml of each of the 13 peptides. The media were changed every three days. The cells were harvested at day 7, total RNA isolated using the Qiagen RNeasy kit and quantified with a spectrophotometer. After initial screening of the genes with real-time PCR, four peptides were chosen for microarray analysis: L13, L19, R1, and R3 (SEQ ID NOs: 8, 10, 11, and 13, respectively). The microarray data showed changes in several genes that are associated with osteogenesis. Table 4 shows upregulated as well as downregulated genes in cells treated with peptide L13 (SEQ ID NO:8).

Example 8

Further Studies of Peptide-Mediated Osteogenesis in Cortical Bone Defects

In an in vivo study, all 13 peptides at a concentration of 100 mM were tested for their ability to potentiate osteogenesis. A gelfoam cylinder 1.5 mm in diameter 2 mm in length was used as carrier for the peptides. Unicortical femoral defects 1.5 mm in diameter were created bilaterally in Fisher 344 rats; the left femoral defect was filled with gelfoam+PBS (Control), and the right femur with gelfoam+peptide. The samples were harvested and examined two weeks postoperatively.

The results showed that peptides R3, R1, L7, R8, L12, and L6 (SEQ ID NOs:13, 11, 5, 14, 7, and 4, respectively) were most effective at stimulating osteogenesis and cortical bone repair. Histologically, a considerable amount of bone had appeared in the cortical defects that were filled with gelfoam+peptide compared with the defects that had been filled with gelfoam+PBS (without peptide) i.e. the control. In addition, the gelfoam+peptide composites effectively produced cortical bone that is thicker and more continuous than the controls.

Figure 5A:
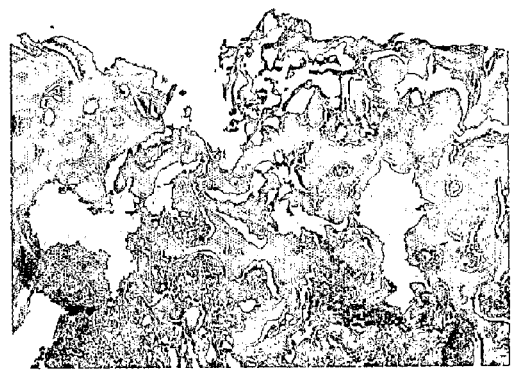
FIGS. 5A, 5B, and 5C, represents photomicrographic images comparing osteogenesis in defects treated with gelfoam+PBS (control, FIG. 5A), gelfoam+R1 peptide (SEQ ID NO:11) (FIG. 5B) and gelfoam+L7 peptide (SEQ ID NO:5) (FIG. 5C). Repair tissue shows considerable amounts of cortical bone in the defects filled with gelfoam containing the peptide R1 (SEQ ID NO:11) or L7 (SEQ ID NO:5). By contrast, the defect filled with gelfoam alone (Control) did not show continuity in cortical bone regeneration.
Figure 5B:
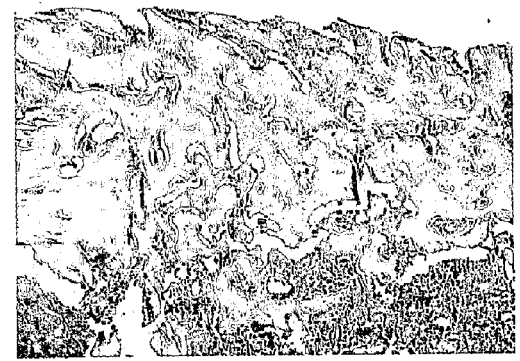
Figure 5C:
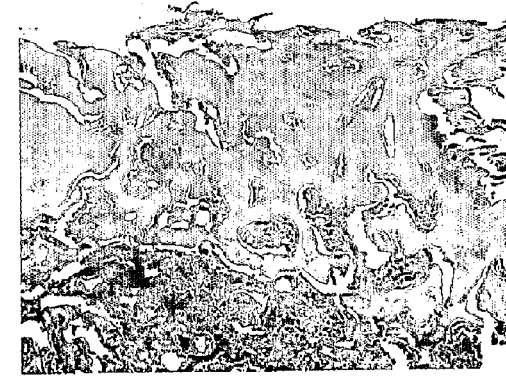
Figure 6A:
FIG. 6, comprising FIGS. 6A (L5; SEQ ID NO:3) and 6B (L19; SEQ ID NO:10), represents photomicrographic images of bone repair following exposure to the peptides L5 (SEQ ID NO:3) and L19 (SEQ ID NO:10). Control versus least osteogenic peptides—while some ossification and cortical bone regeneration has occurred, considerable amounts of gelfoam remains in the defect. Cortical bone is thinner, and the regenerate tissue is loosely organized compared with the cortical bone in FIG. 5.
Figure 6B:
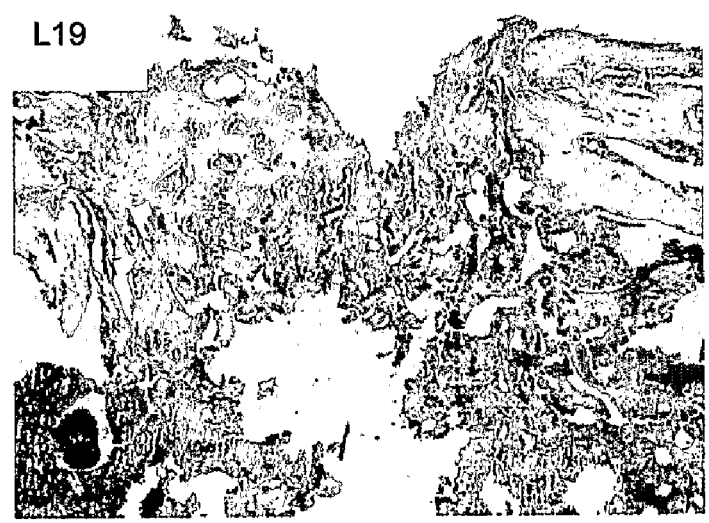

The most effective peptides for osteogenesis and repair of cortical defects are R1 (SEQ ID NO:11) and L7 (SEQ ID NO:5) (FIG. 5). The peptides that were least effective for cortical bone repair were L1, L2, L13, and L14 (SEQ ID NOs:1, 2, 8, and 9, respectively). Defects filled with these peptides showed a considerable amount of gelfoam remaining in the defects, with thinner and more loosely organized cortical bone compared with the most effective peptides, while L5 and L19 had virtually no stimulatory effect on osteogenesis (FIG. 6).

To examine the effect of peptide concentration on cortical bone regeneration, peptide L7 (SEQ ID NO:5) was used at 1, 5, and 20 mM. Osteogenesis was most pronounced with the highest concentration of peptide. The amount of bone that regenerated increased with all the concentrations of peptide, even at 1 mM and 5 mM compared with the controls without peptide.

The time course of cortical bone repair with 20 mM L7 was examined at 5, 10, 15, and 20 days. Cortical bone regeneration increased with time. At every time point, new bone formation was greater in the defects treated with peptide compared with the corresponding controls.

Table 5 provides a summary of representative peptides of the invention with the four amino acid linker consisting of three glycine residues and one serine residue as found on the peptides having SEQ ID NOs: 1-14. Note that the peptides named R2 (SEQ ID NO:12; not shown in Table 5) and L13 (SEQ ID NO:8) have the same sequence.

TABLE 5

Peptides (with the four amino acid residue linker)

| Peptide region designation and SEQ ID NO | Amino acid sequence | Linker |
|---|---|---|
| L1-1 | THR-MET-ARG-ASN-PRO-ILE-THR-SER-LEU-ILE-SER-VAL- <br> T   M   R   N   P   I   T   S   L   I   S   V | GLY-GLY-GLY-SER <br> G   G   G   S |
| L2-2 | LEU-LEU-ALA-ASP-THR-THR-HIS-HIS-ARG-PRO-TRP-THR- <br> L   L   A   D   T   T   H   H   R   P   W   T | GLY-GLY-GLY-SER <br> G   G   G   S |
| L5-3 | LYS-GLU-ILE-PRO-PRO-ILE-PRO-LEU-LEU-ALA-PRO-SER- <br> K   E   I   P   P   I   P   L   L   A   P   S | GLY-GLY-GLY-SER <br> G   G   G   S |
| L6-4 | ASN-ASN-VAL-SER-GLN-LYS-TRP-GLN-GLN-ARG-LEU-ILE- <br> N   N   V   S   Q   K   W   Q   Q   R   L   I | GLY-GLY-GLY-SER <br> G   G   G   S |
| L7-5 | ASN-SER-MET-ILE-ALA-HIS-ASN-LYS-THR-ARG-MET-HIS- <br> N   S   M   I   A   H   N   K   T   R   M   H | GLY-GLY-GLY-SER <br> G   G   G   S |
| L11-6 | GLY-ILE-HIS-VAL-PRO-TRP-MET-PRO-PRO-VAL-ALA-PHE- <br> G   I   H   V   P   W   M   P   P   V   A   F | GLY-GLY-GLY-SER <br> G   G   G   S |
| L12-7 | GLN-ARG-SER-TRP-THR-LEU-ASP-SER-ALA-LEU-SER-MET- <br> Q   R   S   W   T   L   D   S   A   L   S   M | GLY-GLY-GLY-SER <br> G   G   G   S |
| L13-8 | SER-GLY-HIS-GLN-LEU-LEU-LEU-ASN-LYS-MET-PRO-ASN- <br> S   G   H   Q   L   L   L   N   K   M   P   N | GLY-GLY-GLY-SER <br> G   G   G   S |
| L14-9 | SER-SER-THR-LEU-LYS-THR-PHE-PHE-GLY-PHE-PRO-ASP- <br> S   S   T   L   K   T   F   F   G   F   P   D | GLY-GLY-GLY-SER <br> G   G   G   S |
| L19-10 | ASP-SER-SER-ASN-PRO-ILE-PHE-TRP-ARG-PRO-SER-SER- <br> D   S   S   N   P   I   F   W   R   P   S   S | GLY-GLY-GLY-SER <br> G   G   G   S |
| R1-11 | ASN-TYR-SER-HIS-LEU-ARG-VAL-LYS-LEU-PRO-THR-PRO- <br> N   Y   S   H   L   R   V   K   L   P   T   P | GLY-GLY-GLY-SER <br> G   G   G   S |
| R3-13 | ALA-THR-TRP-SER-HIS-HIS-LEU-SER-SER-ALA-GLY-LEU- <br> A   T   W   S   H   H   L   S   S   A   G   L | GLY-GLY-GLY-SER <br> G   G   G   S |
| R8-14 | SER-TYR-SER-GLN-MET-ASP-PRO-PRO-ARG-SER-LEU-PRO- <br> S   Y   S   Q   M   D   P   P   R   S   L   P | GLY-GLY-GLY-SER <br> G   G   G   S |

Without wishing to be bound by any particular theory, the data disclosed herein suggest that R1 (SEQ ID NO:11) and L7 (SEQ ID NO:5) are the most effective peptides for osteogenesis because of the thickness, density, and continuity of cortical bone within the defect.

Summary

Repair of unicortical defects was enhanced by the combination of bone targeting peptides with gelfoam. While gelfoam alone was effective, the addition of peptide at 20 mM and 100 mM showed more bone formation and more continuity of cortical bone in the defects at 2 weeks.

Therefore, the results described herein indicate that the peptides described herein: can prevent the adhesion of bovine endothelial cells; may inhibit angiogenesis; may bind to cellular elements in bone marrow and thereby may have potential cellular targets; and are osteogenic when delivered to bone defects in vivo.

Example 9

Mesenchymal Cells

The present invention further encompasses isolation and characterization of bone marrow mesenchymal cells that are multipotential and are capable of targeting bone marrow upon intravenous administration of genetically labeled cells into host syngeneic mice. This bone marrow homing phenomenon was exploited for the purposes of gene delivery, which can be useful for musculoskeletal gene therapy. We have used genetically modified cells to carry an IGF-1 cDNA, and showed homing of these cells to bone marrow and to fractures of bone. The genetically modified mesenchymal cells were also shown to target sites of injury in the musculoskeletal system such as defects that were created in cortical bone and femur fractures.

Further experiments were carried out exploiting the phenomenon of mesenchymal cell homing to skeletal tissues. Cells transduced with thymidine kinase or cytidine deaminase, killer genes that can be expressed under the influence of a prodrug, lead to a cell kill effect on neighboring prostate cancer cells in a co-culture system in vitro.

In vivo, the mesenchymal cells and prostate cancer cells were co-injected into subcutaneous sites in immune deficient rats. Chimeric tumors formed initially, but diminished in size upon treatment with the prodrug gencyclovir. There was a corresponding drop in serum PSA levels in the treated rats. Therefore, a cell-based gene delivery system may be useful to pursue as potential therapy for metastatic cancer, particularly prostate cancer cells that have spread to bone. Without wishing to be bound by any particular theory, it was hypothesized that from a phage display peptide library of $2.7 \times 10^9$ different peptide sequences one could retrieve phage from bone that displayed unique sequences, and that if the phage were reintroduced into mice that some, if not all, of the bone targeting peptides would be retrievable from bone (in vivo panning). The present invention indeed shows that by in vivo panning, the peptides were found repeatedly in bone and did not reappear in significant amounts in other tissues that were examined such as liver and kidney.

The peptides were ranked based on the frequency with which they occurred in the plaques from which DNA was prepared and sequenced. Four of the sequences (L13, L19, R1, and R3) were synthesized as biotinylated peptide or as the control non biotinylated version of the sequence. Two of the three peptides, L13 (SEQ ID NO:8) and R1, were tested in vitro and were found to bind cells from the skeleton. The cells used in these experiments were mesenchymal cells from bone marrow (D1), or human bone marrow endothelial cells. An avidin-FITC probe detected the biotinylated peptide in areas of the cells in culture representing either extrusions from the cells or at the end of cell processes; structures reminiscent of adhesion plaques or footprints. Biotinylated L13 binds to areas of bone and marrow in cryosections of mouse femur detectable with Avidin-FITC (see FIGS. 7A and 7B). Similarly, L13 binds to fresh frozen sections of mouse rib containing bone and marrow cells (see FIGS. 7C and 7D).

A similar system using avidin tagged with a chemiluminescent probe was used to detect peptide binding to cell lysates that were fractionated into cytosolic or cell membrane fractions. The highest intensity of chemiluminescence was found in the cell membrane fraction. One of the biotinylated peptides that binds to avidin-agarose was used for affinity chromatography to identify ligands in the plasma membrane fractions. Two proteins were identified by gel electrophoresis in sufficient quantity for sequencing. The protein sequence of one was identical to nucleolin.

Two dimensional gel electrophoresis has been used successfully to separate cell membrane and extracellular matrix proteins from cultures of bone marrow mesenchymal cells. Such adhesion properties are reminiscent of tumor cell attachment and invasion and they are taken into consideration in discussions of cancer cell metastases to bone. The prostate literature is replete with references stating the dramatic tendency for CaP metastases within the marrow forming centers of bone. Assays were established to test directly whether this proclivity is due to an inherent adhesive preference for bone marrow stromal or endothelial cells by more aggressive prostate cancer cells.

The studies showed that with CaP cell adhesion to bone stromal cells (D1) and human bone marrow endothelial cells (BMEC) have shown that the less aggressive cells actually adhere better than the more aggressive cells, in contrast to what might be predicted based on the literature. A cell with strong adhesive properties would be less likely to metastasize while a metastatic cell must achieve a balance between adhesivity and motility. Nevertheless, the interference of adhesion remains a viable target in the prevention of metastasis. This is because, for a cell to invade the tissue and establish a metastasis it must still bind the target at some frequency.

Example 10

Effects on Cancer Cells

Figure 8:
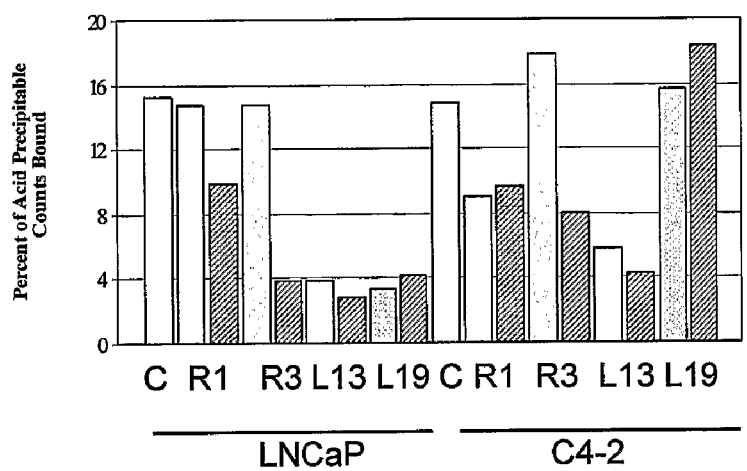
FIG. 8 is a graphic representation of the effects of various peptides on altering cellular adhesion to BMEC cells in vitro. LNCaP cells were compared directly to C4-2 cells for the ability of specific phage-derived peptides to alter cellular adhesion to BMEC cells in vitro. Adhesion was measured at hours. C=control (no peptide). The ordinate represents percent of acid precipitable counts bound and the abscissa indicated the cells treated and the peptides used.

The phage-derived bone-targeting peptides isolated by biopanning were tested for their ability to alter the adhesion of prostate cancer cells to a human bone marrow endothelial cell line (see FIG. 8). In this assay, LNCaP cells were compared directly to the more metastatic, bone colonizing derivative, C4-2. These preliminary results show the possibility that the phage-derived peptides may have specific responses towards CaP cell adhesion. In this assay the peptide R1 did not show remarkable activity while R3 showed a dose-dependent inhibition of CaP cell invasion for both cell lines.

The peptide, L13 (SEQ ID NO:8), showed consistent suppression of CaP cell invasion that was saturated at the doses tested. L19 (SEQ ID NO:10), on the other hand, showed a remarkable difference between LNCaP and C4-2 cells. Remarkably, this peptide (L19) strongly inhibited the less aggressive LNCaP cell while leaving the adhesion of the C4-2 cell line unaffected. These results demonstrate that the phage-derived peptides have some cell type and dose-dependent activity.

Figure 9:
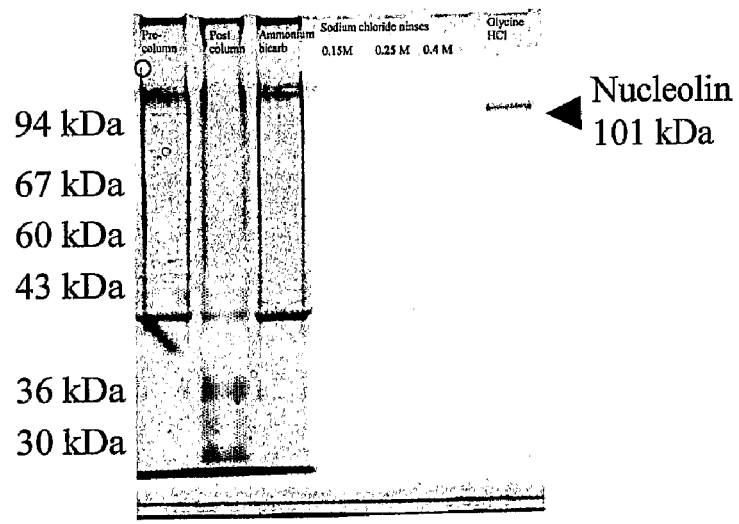
FIG. 9 is a representation of an electrophoretic analysis of fractions obtained by chromatography of bone marrow endothelial cells on immobilized peptide L13. Nucleolin (101 kDa) was identified in the HCl-glycine eluate.

An experiment was performed to detect proteins solubilized from BMEC that are retained on a peptide affinity column designed using one of the peptide sequences. Cell membranes from BMEC were solubilized with lysis buffer and then loaded onto the peptide affinity column. Following extensive washes with buffer, the retained proteins were eluted with a buffer containing increasing concentrations of NaCl. This eluant was concentrated and analyzed by SDS PAGE (see FIG. 9). One band at 101 kDa was analyzed by LC/MS/MS and identified as nucleolin. The significance of finding nucleolin in solubilized cell membranes and its retention on the peptide affinity column is the subject of the proposed investigation.

A second experiment demonstrated the approach that bone marrow cell membrane proteins can be identified. In this experiment protein from solubilized cells were analyzed by 2D PAGE. One gel was silver stained and the other was electroblotted onto a PVDF membrane. The blotted proteins were re-natured by soaking the membrane in triton X-100 and then washed in PBS. The PVDF membrane was then treated with biotinylated peptide, washed and then the presence of bound peptide detected by SA-antibody and ECL. Two spots were developed on the PVDF. The positions of the spots were correlated with stained spots on the 2D gel. Those spots in the 2D gel were excised, digested, and analyzed by LC/MS/MS for identification. One spot identified in this manner was annexin I and the other was type VI collagen α1.

Both experimental approaches were able to identify proteins solubilized from bone marrow cell membranes that could interact with peptides that had previously been demonstrated from phage display to confer bone marrow tropism to the phage in the mouse model. Without wishing to be bound by any particular theory, it is believed that these experiments prove the capability of these approaches and are critical for future experiments to confirm the specificity of the interaction of these peptides, and potentially proteins that contain these sequences.

Peptide Affinity Column Chromatography: Peptides identified from the phage display experiments in mouse bone and bone marrow were synthesized with an additional three-residue glycine linker and an N-terminal lysine residue. The lysine residue was used to specifically link the peptides to a support. Cell membranes from BMECs were solubilized with triton X-100. The solubilized proteins were passed through the peptide affinity column (total volume, 500 µL) followed by extensive washes with buffer. Retained proteins were eluted either with 100 mM solution of the same peptide as that immobilized on the column or with a wash of 0.1 N HCl-Glycine, pH 2.2. The eluates were analyzed by SDS PAGE and proteins observed in the gels were identified by LC/MS/MS.

Nucleolin: The data disclosed herein show that nucleolin is one of the cellular components that can be isolated by affinity chromatography on synthetic peptide. Gel electrophoresis of components prepared from cell membranes showed a number of bands. The amino acid sequence of the band eluted with HCl-Glycine, i.e. the component with the highest affinity to the immobilized peptide, corresponded to nucleolin. The experiments demonstrate the capability to perform affinity chromatography utilizing biotinylated phage display library peptides that are immobilized on avidin-agarose.

With sections of different tissue using biotinylated peptides, it was found that a 1/50,000 dilution of Avidin-FITC revealed significant binding to rib and long bone growth plate by both L13 (SEQ ID NO:8) and R1 (SEQ ID NO:11). By contrast, R3 (SEQ ID NO:13) peptide showed no staining. These experiments demonstrated the specificity of some of the peptides, and that binding properties to bone and to marrow is not shared by all of the peptides isolated from the phage display library. Furthermore, these peptides inhibit prostate cancer cell adhesion to BMEC, R3 (SEQ ID NO:13) at 100 µM only, and L13 (SEQ ID NO:8) at both 50 µM and 100 µm. The binding characteristics of these biotinylated peptides to bone marrow as detected by fluorescence microscopy using Avidin-FITC are consistent with the observations that L13 inhibits CaP cell adhesion to bone marrow endothelial cells. This observation will be examined further and exploited by the aims of this proposal to identify the binding partners of nucleolin in prostate cancer cells as well as to investigate bone tropic peptides as potential inhibitors of prostate cancer metastasis.

Other methods which were used but not described herein are well known and within the competence of one of ordinary skill in the art of cell biology and molecular biology.

The invention should not be construed to be limited solely to the assays and methods described herein, but should be construed to include other methods and assays as well. One of skill in the art will know that other assays and methods are available to perform the procedures described herein.

Headings are included herein for reference and to aid in locating certain sections. These headings are not intended to limit the scope of the concepts described therein under, and these concepts may have applicability in other sections throughout the entire specification.

The disclosures of each and every patent, patent application, and publication cited herein are hereby incorporated herein by reference in their entirety.

While this invention has been disclosed with reference to specific embodiments, it is apparent that other embodiments and variations of this invention may be devised by the previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

What is claimed is:

1. A method of identifying a binding partner of a bone-targeting peptide, wherein said peptide comprises the amino acid sequence selected from the group consisting of SEQ ID NOs:29 and 30, said method comprising contacting said peptide with a subcellular fraction derived from a cell or tissue of interest under conditions to allow binding of said peptide with said binding partner, washing away unbound material from the subcellular fraction, isolating the bound material from said peptide, and characterizing said isolated bound material, thereby identifying a binding partner of a peptide of the invention.

2. The method of claim 1, wherein said peptide is bound to a solid support.

3. The method of claim 2, wherein said binding partner is nucleolin or vimentin.

4. An isolated nucleic acid comprising a nucleic acid sequence encoding a peptide comprising the amino acid sequence selected from the group consisting of SEQ ID NOs: 29 and 30.

5. A kit for administering a peptide comprising the amino acid sequence selected from the group consisting of SEQ ID NOs:29 and 30, said kit comprising a pharmaceutical composition comprising at least one of said peptides, an applicator, and an instructional material for the use thereof.

* * * * *

SEQUENCE LISTING

```
<160> NUMBER OF SEQ ID NOS: 30

<210> SEQ ID NO 1
<211> LENGTH: 16
<212> TYPE: PRT
<213> ORGANISM: Homo sapiens

<400> SEQUENCE: 1

Thr Met Arg Asn Pro Ile Thr Ser Leu Ile Ser Val Gly Gly Gly Ser
1               5                   10                  15
```

-continued

<210> SEQ ID NO 2
<211> LENGTH: 16
<212> TYPE: PRT
<213> ORGANISM: Homo sapiens

<400> SEQUENCE: 2

Leu Leu Ala Asp Thr Thr His His Arg Pro Trp Thr Gly Gly Gly Ser
1               5                   10                  15

<210> SEQ ID NO 3
<211> LENGTH: 16
<212> TYPE: PRT
<213> ORGANISM: Homo sapiens

<400> SEQUENCE: 3

Lys Glu Ile Pro Pro Ile Pro Leu Leu Ala Pro Ser Gly Gly Gly Ser
1               5                   10                  15

<210> SEQ ID NO 4
<211> LENGTH: 16
<212> TYPE: PRT
<213> ORGANISM: Homo sapiens

<400> SEQUENCE: 4

Asn Asn Val Ser Gln Lys Trp Gln Gln Arg Leu Ile Gly Gly Gly Ser
1               5                   10                  15

<210> SEQ ID NO 5
<211> LENGTH: 16
<212> TYPE: PRT
<213> ORGANISM: Homo sapiens

<400> SEQUENCE: 5

Asn Ser Met Ile Ala His Asn Lys Thr Arg Met His Gly Gly Gly Ser
1               5                   10                  15

<210> SEQ ID NO 6
<211> LENGTH: 16
<212> TYPE: PRT
<213> ORGANISM: Homo sapiens

<400> SEQUENCE: 6

Gly Ile His Val Pro Trp Met Pro Pro Val Ala Phe Gly Gly Gly Ser
1               5                   10                  15

<210> SEQ ID NO 7
<211> LENGTH: 16
<212> TYPE: PRT
<213> ORGANISM: Homo sapiens

<400> SEQUENCE: 7

Gln Arg Ser Trp Thr Leu Asp Ser Ala Leu Ser Met Gly Gly Gly Ser
1               5                   10                  15

<210> SEQ ID NO 8
<211> LENGTH: 16
<212> TYPE: PRT
<213> ORGANISM: Homo sapiens

<400> SEQUENCE: 8

Ser Gly His Gln Leu Leu Leu Asn Lys Met Pro Asn Gly Gly Gly Ser
1               5                   10                  15

```
<210> SEQ ID NO 9
<211> LENGTH: 16
<212> TYPE: PRT
<213> ORGANISM: Homo sapiens

<400> SEQUENCE: 9

Ser Ser Thr Leu Lys Thr Phe Phe Gly Phe Pro Asp Gly Gly Gly Ser
1               5                   10                  15

<210> SEQ ID NO 10
<211> LENGTH: 16
<212> TYPE: PRT
<213> ORGANISM: Homo sapiens

<400> SEQUENCE: 10

Asp Ser Ser Asn Pro Ile Phe Trp Arg Pro Ser Ser Gly Gly Gly Ser
1               5                   10                  15

<210> SEQ ID NO 11
<211> LENGTH: 16
<212> TYPE: PRT
<213> ORGANISM: Homo sapiens

<400> SEQUENCE: 11

Asn Tyr Ser His Leu Arg Val Lys Leu Pro Thr Pro Gly Gly Gly Ser
1               5                   10                  15

<210> SEQ ID NO 12
<211> LENGTH: 16
<212> TYPE: PRT
<213> ORGANISM: Homo sapiens

<400> SEQUENCE: 12

Ser Gly His Gln Leu Leu Leu Asn Lys Met Pro Asn Gly Gly Gly Ser
1               5                   10                  15

<210> SEQ ID NO 13
<211> LENGTH: 16
<212> TYPE: PRT
<213> ORGANISM: Homo sapiens

<400> SEQUENCE: 13

Ala Thr Trp Ser His His Leu Ser Ser Ala Gly Leu Gly Gly Gly Ser
1               5                   10                  15

<210> SEQ ID NO 14
<211> LENGTH: 16
<212> TYPE: PRT
<213> ORGANISM: Homo sapiens

<400> SEQUENCE: 14

Ser Tyr Ser Gln Met Asp Pro Pro Arg Ser Leu Pro Gly Gly Gly Ser
1               5                   10                  15

<210> SEQ ID NO 15
<211> LENGTH: 12
<212> TYPE: PRT
<213> ORGANISM: Homo sapiens

<400> SEQUENCE: 15

Thr Met Arg Asn Pro Ile Thr Ser Leu Ile Ser Val
1               5                   10

<210> SEQ ID NO 16
<211> LENGTH: 12
```

```
<212> TYPE: PRT
<213> ORGANISM: Homo sapiens

<400> SEQUENCE: 16

Leu Leu Ala Asp Thr Thr His His Arg Pro Trp Thr
1               5                   10

<210> SEQ ID NO 17
<211> LENGTH: 12
<212> TYPE: PRT
<213> ORGANISM: Homo sapiens

<400> SEQUENCE: 17

Lys Glu Ile Pro Pro Ile Pro Leu Leu Ala Pro Ser
1               5                   10

<210> SEQ ID NO 18
<211> LENGTH: 12
<212> TYPE: PRT
<213> ORGANISM: Homo sapiens

<400> SEQUENCE: 18

Asn Asn Val Ser Gln Lys Trp Gln Gln Arg Leu Ile
1               5                   10

<210> SEQ ID NO 19
<211> LENGTH: 12
<212> TYPE: PRT
<213> ORGANISM: Homo sapiens

<400> SEQUENCE: 19

Asn Ser Met Ile Ala His Asn Lys Thr Arg Met His
1               5                   10

<210> SEQ ID NO 20
<211> LENGTH: 12
<212> TYPE: PRT
<213> ORGANISM: Homo sapiens

<400> SEQUENCE: 20

Gly Ile His Val Pro Trp Met Pro Pro Val Ala Phe
1               5                   10

<210> SEQ ID NO 21
<211> LENGTH: 12
<212> TYPE: PRT
<213> ORGANISM: Homo sapiens

<400> SEQUENCE: 21

Gln Arg Ser Trp Thr Leu Asp Ser Ala Leu Ser Met
1               5                   10

<210> SEQ ID NO 22
<211> LENGTH: 12
<212> TYPE: PRT
<213> ORGANISM: Homo sapiens

<400> SEQUENCE: 22

Ser Gly His Gln Leu Leu Leu Asn Lys Met Pro Asn
1               5                   10

<210> SEQ ID NO 23
<211> LENGTH: 12
<212> TYPE: PRT
<213> ORGANISM: Homo sapiens
```

```
<400> SEQUENCE: 23

Ser Ser Thr Leu Lys Thr Phe Phe Gly Phe Pro Asp
1               5                   10

<210> SEQ ID NO 24
<211> LENGTH: 12
<212> TYPE: PRT
<213> ORGANISM: Homo sapiens

<400> SEQUENCE: 24

Asp Ser Ser Asn Pro Ile Phe Trp Arg Pro Ser Ser
1               5                   10

<210> SEQ ID NO 25
<211> LENGTH: 12
<212> TYPE: PRT
<213> ORGANISM: Homo sapiens

<400> SEQUENCE: 25

Asn Tyr Ser His Leu Arg Val Lys Leu Pro Thr Pro
1               5                   10

<210> SEQ ID NO 26
<211> LENGTH: 12
<212> TYPE: PRT
<213> ORGANISM: Homo sapiens

<400> SEQUENCE: 26

Ser Gly His Gln Leu Leu Leu Asn Lys Met Pro Asn
1               5                   10

<210> SEQ ID NO 27
<211> LENGTH: 12
<212> TYPE: PRT
<213> ORGANISM: Homo sapiens

<400> SEQUENCE: 27

Ala Thr Trp Ser His His Leu Ser Ser Ala Gly Leu
1               5                   10

<210> SEQ ID NO 28
<211> LENGTH: 16
<212> TYPE: PRT
<213> ORGANISM: Homo sapiens

<400> SEQUENCE: 28

Ser Tyr Ser Gln Met Asp Pro Pro Arg Ser Leu Pro Gly Gly Gly Ser
1               5                   10                  15

<210> SEQ ID NO 29
<211> LENGTH: 16
<212> TYPE: PRT
<213> ORGANISM: homo sapiens

<400> SEQUENCE: 29

Leu Pro Trp Thr Glu Pro Ser Phe Trp Arg Thr Pro Gly Gly Gly Ser
1               5                   10                  15

<210> SEQ ID NO 30
<211> LENGTH: 12
```

```
-continued

<212> TYPE: PRT
<213> ORGANISM: homo sapiens

<400> SEQUENCE: 30

Leu Pro Trp Thr Glu Pro Ser Phe Trp Arg Thr Pro
1               5                   10
```